US010681907B2

(12) United States Patent
Robinson

(10) Patent No.: US 10,681,907 B2
(45) Date of Patent: Jun. 16, 2020

(54) USE OF TREE SAP TO PRESERVE SPERM CELL LINES

(71) Applicant: CRYOSAPS, LLC, Waterford, WI (US)

(72) Inventor: Meg A. Robinson, Waterford, WI (US)

(73) Assignee: Meg Ann Robinson, Family Trust Dated Jun. 1, 2016

( * ) Notice: Subject to any disclaimer, the term of this patent is extended or adjusted under 35 U.S.C. 154(b) by 256 days.

(21) Appl. No.: 15/569,164

(22) PCT Filed: Apr. 26, 2016

(86) PCT No.: PCT/US2016/029351
§ 371 (c)(1),
(2) Date: Oct. 25, 2017

(87) PCT Pub. No.: WO2016/176200
PCT Pub. Date: Nov. 3, 2016

(65) Prior Publication Data
US 2018/0146659 A1 May 31, 2018

Related U.S. Application Data

(60) Provisional application No. 62/153,197, filed on Apr. 27, 2015.

(51) Int. Cl.
*A01N 1/02* (2006.01)
*C12N 5/076* (2010.01)

(52) U.S. Cl.
CPC ......... *A01N 1/0221* (2013.01); *A01N 1/0284* (2013.01); *C12N 5/061* (2013.01)

(58) Field of Classification Search
CPC ................ A01N 1/0221; A01N 1/0284; A01N 1/00–0294; C12N 5/061; A61B 17/42–48; A61H 19/00–50
See application file for complete search history.

(56) References Cited

U.S. PATENT DOCUMENTS

2003/0186212 A1  10/2003  Loskutoff et al.
2013/0189669 A1   7/2013  Ostermeier et al.

OTHER PUBLICATIONS

The International Search Report and Written Opinion as dated Aug. 11, 2016 for International Application No. PCT/US2016/029351.
Deslauriers et al., Recovery, separation and characterization of phenolic compounds and flavonoids from maple product, Mar. 2000, Thesis, McGill University [Retrieved on Jul. 5, 2016] Retrieved from website <URL: http://digitool.library.mcgill.ca/R/?func=dbin-jump-full&object_id=30366&local_base=GEN01-MCGO2> p. 13, para. 4.
Forbes, "Captive raptor propagation", Aug. 22, 2009 [online] [Retrieved on Jul. 5, 2016] Retrieved from website <URL: http://www.gwexotics.com/wccms-resources/2/8/1/d/ea912162-9da4-11e0-a685-005056862ea.pdf> p. 1, para. 3: p. 2, para. 1: Table 2; p. 11, para. 2; p. 12, para. 3.

*Primary Examiner* — Thaddeus B Cox
(74) *Attorney, Agent, or Firm* — Quarles & Brady LLP

(57) ABSTRACT

A method of cryogenically preserving sperm comprising (a) combining sperm to be cryogenically preserved and a composition that comprises (1) a cryoprotectant, comprising one or more tree saps; and (2) an extender medium to produce a sperm/medium combination; and (b) subjecting the combination to conditions that result in cryopreservation of sperm, thereby producing a cryopreserved combination that comprises cryopreserved sperm is disclosed.

22 Claims, No Drawings

USE OF TREE SAP TO PRESERVE SPERM CELL LINES

CROSS-REFERENCE TO RELATED APPLICATIONS

This application represents the national stage entry of PCT International Application No. PCT/US2016/029351 filed on Apr. 26, 2016 and claims priority to U.S. patent application Ser. No. 62/153,197, filed Apr. 25, 2015 and, the contents of which are incorporated by reference as if set forth in their entirety herein.

STATEMENT REGARDING FEDERALLY SPONSORED RESEARCH OR DEVELOPMENT

N/A

BACKGROUND

In general, the present invention involves the use of tree sap to cryogenically preserve avian and mammalian sperm cells, preferably for use in the poultry industry, birds of prey preservation, and preservation of endangered or threatened avian species. The present invention may also be used in the cattle industry, pig industry, equine industry, and in mammalian veterinary medicine.

Avian spermatozoa have a shape that makes the spermatozoa hard to freeze. The spermatozoa are long and thin and are shaped like a whip. This makes the cells very subject to cryogenic injury because they have a large surface area that can be damaged easily upon freezing or processing. Mammalian sperm will also benefit from the present invention because even though these cells are easier to freeze, they are still subject to damage from the cryogenic processes. (Reference; Avian Semen Cryopreservation: What Are the Biological Challenges? J. A. Long, 2006 Biotechnology and Germplasm Laboratory, Animal and Natural Resources Institute, Beltsville Agricultural Research Center, Agricultural Research Service, USDA, Beltsville, Md. 20705, 2006 Poultry Science Association, Inc. Accepted Sep. 10, 2005)

Currently, avian spermatozoa are frozen using several techniques. One technique uses the addition of a cryoprotectant to a fluid media that suspends and supports the cells. The first step in the procedure is to collect the semen and then add a liquid extender. A semen extender is a liquid diluent which is added to semen to preserve its fertilizing ability. The extender allows the semen to be freighted to the female, rather than requiring the male and female to be near to each other. Special freezing extender also allows cryogenic preservation of sperm ("frozen semen"), which may be transported for use, or used on-site at a later date.

This extender/cell mixture is then placed in a refrigerator to chill the mixture down to a desired temperature that allows the cells to line up the lipid components in their outer cell membrane prior to freezing. This is a form of "cold acclimation" and helps to allow the cells to survive the cryogenic process. The method also reduces the temperature gradient drop that the cells have to go through before they reach the freezing point and reduces the cell damage when being frozen.

Once the cells are chilled/acclimated, the cryoprotectant is added to the extender/cell mix, the mixture is packaged quickly and either flash frozen by quick immersion in the liquid nitrogen, pelletized and flash frozen and then packaged into cryo-vials, or suspended above the liquid nitrogen in the vapors to freeze more slowly before it is immersed in the liquid nitrogen. Both fast and slow freezing can be done based on species requirements. Different cryoprotectants that are added to the mix commonly include DMSO (Dimethyl sulfoxide), MA (Methyl-Acetamide), and DMA (Dimethyl Acetamide). These chemicals act as intracellular cryoprotectants while the non-cell wall-permeable chemicals act as extracellular cryoprotectants. These are also known to damage the cell wall during cryopreservation and this impairs fertility.

A better and more effective way of preserving avian and mammalian semen is needed in the art.

SUMMARY OF THE INVENTION

In one embodiment, the present invention is a method of cryogenically preserving sperm comprising (a). combining sperm to be cryogenically preserved and a composition that comprises (1) a cryoprotectant, comprising one or more tree saps; and (2) an extender medium to produce a sperm/medium combination and (b). subjecting the combination to conditions that result in cryopreservation of sperm, thereby producing a cryopreserved combination that comprises cryopreserved sperm. In one version of the invention the sperm is avian sperm. In one version the sperm is derived from the Northern goshawk (*Accipiter gentilis*).

In another version of the invention the sperm is derived from a mammalian non-human species, preferably selected from the group consisting of cattle, pigs and equines.

In one version of the invention the sap is either maple tree sap or birch tree, preferably both first run saps.

In one version, the present invention is the cryopreserved combination resulting from the method described above.

In another version, the present invention is a method of fertilizing an egg cell comprising the step of introducing the combination described above to an unfertilized egg cell, wherein the egg becomes fertilized.

DESCRIPTION OF THE INVENTION

In general, the present invention is a method and medium useful for the cryogenic preservation of sperm using tree saps. In another embodiment, the present invention is a composition comprising the mixture of the preservation medium and the sperm, using tree saps.

Although the present invention is useful for all animal sperm, the invention is most preferably used with avian sperm because of the special physiologic needs of the avian samples. Preferred avian species include birds of prey (such as *Falconiforms* and *Strigiformes*) and commercial species such as turkeys, chickens (*Galliformes*) and ducks (*Anseriformes*.) Other preferred avian species include but are not limited to *Passeriformes* and *Psittacifomes*.

In another version of the invention, one may wish to preserve the sperm of other mammalian species, including cattle (Family—Bovidae), pigs (Family—Suidae), horses (Family—Equidae) and veterinary medicine applications, including canine (Canidae) and feline (Felidae) species.

In certain embodiments, the method of cryogenically preserving sperm comprises: (a) combining sperm to be cryogenically preserved with a medium comprising (1) a cryoprotectant, such as one or more tree saps or its extracts; and (2) an extender designed to support cell life, wherein the combination produces a sperm/medium combination (cryoprotective medium/sperm combination); and (b) subjecting the combination to conditions that result in cryopreservation of sperm, thereby producing a cryopreserved combination that comprises cryopreserved sperm.

The typical sperm extender typically contains chemicals to both stabilize and protect cell membranes. The Examples below use Beltsville Turkey Extender (BTE) recipe with the exception of removing fructose as one of the ingredients. The fructose was replaced with sucrose and constitutes a separate extender recipe, also a preferred embodiment of the present invention. It was found that goshawk semen did not do well with fructose as its energy source when being cryogenically preserved. This observation is true for other animal cell lines.

The preferred extender recipe for goshawk semen, and other typical avian semen samples, consists of;
Potassium Diphosphate 3H2O 12.7 grams
Sodium glutamate 8.675 grams
Sucrose to replace Fructose (Anhydrous) 5.000 grams
Sodium Acetate 3 H2O 4.255 grams
TES 1.95 grams
N-tris Hydroxymethyl Methyl-2Amino-ethane Sulfonic Acid
Potassium citrate 0.64 grams
Potassium Monophosphate 0.65 grams
Magnesium Chloride 0.338 grams
Purified water 1022 ml is added to the dry ingredients.

This constitutes a full recipe of the preferred extender for goshawk semen for cryopreservation. The sucrose is often left out of this recipe and supplied just through the addition of tree saps that naturally have sucrose in them. Other base recipes may be preferred for other cell lines in other species to meet those species specific requirements. The sugar supplied for the recipe may come from the sap as in the Examples list in the Excel Spreadsheet.

The present invention involves the use of tree sap as a cryoprotectant. Tree sap is a fluid transported in xylem cells (tracheids or vessel elements) or phloem sieve tube elements of a plant. Two kinds of sap are defined as either Xylem sap or Phloem sap. We include both kinds of sap in our definition.

Tree sap is produced at a time of the year when the trees are going through cold stress and freezing in the temperature ranges that are most harmful to the cells that we are trying to freeze. The trees survive temperatures from freezing to minus 60° F. The trees also survive the daily shift in temperatures that the tree can survive both well above freezing to well below it. The tree sap contains properties that allow it to support cell life even when frozen and when going through rigorous freeze thaw cycles and daily temperature extremes. It contains various sugars, antifreeze proteins, carbohydrates, minerals, phenolic compounds, and other compounds that provide cryoprotective properties. Some of these compounds have yet to be described.

The tree species that are most useful in this invention includes the cold-hardy maple tree species, birch tree species, poplar tree species, aspen tree species, and other trees that can be tapped or where chemicals or fluids can be extracted from them. Tree species from the higher latitude deciduous forests are included even if not listed directly herein.

A common factor in these trees is the amount of sugar in the sap. Sugars have cryoprotective properties. Some avian extender recipes often call for 0.5% of either sucrose or fructose. Most tree species meet or exceed this percentage sugar requirement. Maple tree range anywhere from approximately 0.5% to 4.0% sucrose. Another common factor that these trees have is that they have non-sugar cryoprotectant chemicals in their sap. These chemical may provide stronger cryoprotective properties than that the simple sugars that are easily measured.

There are over 128 species of maple trees worldwide. The sugar maple (*Acer saccharum*) and black maple (*Acer nigrum*) produce the most sugar in their saps. The red maple (*Acer rubrum*) and the silver maple (*Acer saccharinum*) produce less sugar but are in the latitudes where they will likely contain similar cryoprotective properties in their sap. These later two species are one preferred version of the present invention due to the lower sugar content and potentially higher cryoprotective properties in the sap that are not from sugars.

Birch tree (Family—Betulaceae, Genus—*Betula*), poplar tree (Family Salicaceae, Genus—*Populus*), and aspen tree (Family—Salicaceae, Genus—*Populus*) species come from higher latitudes in the United States and Canada and have lower sugar content in their sap than the maple (*Acer* species) tree species do. The non-sugar cryoprotective chemicals in their sap will likely be higher as these species survive in a more extreme environment with temperature ranges fluxuating widely below freezing, and the trees have a lower content of the sugars that are known to be cryoprotective in their sap.

Twenty three species of trees that can be tapped in the United States and are useful in the present invention include but are not limited to Sugar Maple (*Acer saccharum*), Black Maple (*Acer nigrum*), Red Maple (*Acer rubrum*), Silver Maple (*Acer saccharinum*), Norway Maple (*Acer platanoides*), Boxelder (*Acer negundo*), Bigleaf Maple (*Acer macrophyllum*), Canyon Maple or Big Tooth Maple (*Acer grandidentatum*), Rocky Mountain Maple (*Acer glabrum*), Gorosoe (*Acer mono*), Butternut or White Walnut (*Juglans cinerea*), Black Walnut (*Juglans nigra*), Heartnut (*Juglans ailantifolia*), English walnut (*Juglans regia*), Paper Birch (*Betula papyrifera*), Yellow Birch (*Betula alleghaniensis*), Black Birch (*Betula lenta*), River Birch (*Betula nigra*), Gray Birch (*Betula populifolia*), European White Birch (*Betula pendula*), Sycamore (*Platanus occidentalis*), *Acer ginnala*, and Ironwood or hophornbeam (*Ostrya virginiana*).

Preferably, one would begin with extender recipes designed for the preservation or storage of animal sperm. Typically, the initial amount of sap added to the modified extender recipe will make the initial solution physiologically close to the osmolality of the raw semen and still provide for cryo-protection of the cells. The initial osmolality range needed is determined by the measurement of the osmolality of the raw semen.

Goshawk semen has an osmolality of about 341 miliosmoles. Later additions of extender/sap combinations increase the osmolality of the mixture to dehydrate the cells immediately prior to freezing. Dehydrating the cells just prior to freezing them, increases survival.

An ideal osmolality level is determined by the end results of the survival of the cells in question and the ability of the stored sample to create fertile female gametocytes. It is known that different species of birds have sperm cells that tolerate different osmolality extremes. Some avian spermatozoa survive very high osmolality and others do not. [See Species Variation in Osmotic, Cryoprotectant, and Cooling Rate Tolerance in Poultry, Eagle, and Peregrine Falcon Spermatozoa; Juan M. Blanco, George Gee, David E. Wildt, and Ann M. Donoghue; Biology of Reproduction Oct. 1, 2000 vol. 63 no. 4 1164-1171] The use of the sap allows both the removal of other toxic cryoprotectants from the mix and/or reduces the amount of toxic cryoprotectants used. Yet, one may still wish to add additional cryoprotectants to the mix.

A typical sperm/sap-extender combination of the present invention is as follows: The final volume of the sperm/sap-extender combination should be no more than 1:3 dilutions making the semen a quarter of the final volume. Semen dilutions higher than this can impair fertility because of simple dilution.

In a preferred version of the invention, sap comprises at least 30% of the final sperm/extender combination. In another version of the invention, sap comprises 10%-80% of the final sperm/extender combination, preferably about 50%.

Over dilution reduces sperm fertility of the sample. The amount of sap needed to provide cryogenic protection to the mixture varies considerably because of tree species variation in cryoprotectant types and properties.

I have been modifying the extender recipe enough to allow sap to be blended into the mix so that this mix then supports the cells when they are frozen in liquid nitrogen ($LN_2$) with or without the use of an additional cryoprotectant. A typical example of extender includes the dry ingredients of the Beltsville Turkey Extender without the fructose (BTE minus fructose) as a base recipe to work with.

The sap from the Maple tree and the Birch tree were then added to the BTE minus fructose and used at different ratios, to preserve the sperm cells. A recipe that preserved the cells in $LN_2$ well included 1 part raw semen, 1 part BTE minus fructose with 0.5% sucrose added back in, 2 parts BTE minus fructose with sap added, to supply its liquid volume. The sperm and the BTE minus fructose with 0.5% sucrose added back in; were mixed in a 0.5 ml Eppendorf vial in the fridge. A matching volume of BTE minus fructose with sap as its liquid diluent was also placed in the fridge but in a separate tube. Both tubes were allowed to equilibrate to an equal temperature for 10 minutes before they were then mixed, packaged, and then flash frozen. The work was done in the fridge at 42° F. so there were no temperature fluxuations to stress the semen. This form of cold "acclimation" allowed the lipid component of the cell wall to line up prior to freezing to help prevent damage to the cell structure.

Therefore, a preferred version of the present invention comprises a composition, wherein 1 part of the volume is raw semen; 1 part of the volume is extender, such as BTE no fructose plus 0.5% sucrose added back in; and 2 parts of the total volume was BTE no fructose with sap of either the maple or birch tree. A minimum of 50% sap by volume should preferably be used in this mix. Samples with 50% sap by volume had far better survival on thaw than samples with less than this percentage.

The packaging consisted of the semen being placed in a 75 ul Mylar coated capillary tube with one end being caulked. Its opposite end was left open. This capillary tube was then placed inside a standard plastic poultry straw and the end opposite of the cotton was crimped shut. The poultry straw was then placed inside a plastic soda straw that had holes cut in the side of it. These holes allowed the $LN_2$ to enter and surround the poultry straw quickly as it was immersed. The holes in the soda straw also allowed the package to drain and breathe as it was thawed so that it did not explode.

Cryopreservation can be carried out at any time after production of the medium/sperm combination as long as the storage does not significantly adversely affect the viability of the sperm. For example, cryopreservation can often be carried out as long as 180 minutes after the sperm/medium combination is produced with no loss of fertility. Samples should be chilling to extend the shelf life before freezing. A typical temperature for storing avian semen at is 5° C. Chilling the semen helps to line up the lipid component in the cell wall prior to freezing. This increases cell survival.

Preservation is typically carried out at a temperature minus −198° C. In specific embodiments, cryopreservation is carried out at a temperature between from about minus −80° C. to about minus −198° C. In one preferred embodiment, the cryo-protection takes place in a liquid nitrogen bath/canister and the vials are stored at a −198° C. Long term storage can be achieved by placing the storage vials or straws in a liquid nitrogen canister. One would then wish to use the preserved sperm to fertilize a female gametocyte, female germ cell or ovum.

Before the sperm is used for artificial insemination or incubated with a female gamete, the sperm is typically thawed and may also be washed. Sperm samples are often thawed in cold water or warm water baths with the temperature requirements being determined both by the species cell requirements or the cryoprotectant type used in the mix. Avian spermatozoa are typically thawed in ice water baths or cool water baths, and bovine spermatozoa are typically thawed in warm water baths that are body temperature. Insemination is performed immediately after thaw. Sperm are sometimes concentrated into pellets with the contents of different straws being combined, centrifuged down, to form a pellet of semen.

In all embodiments described herein, the resulting cryopreserved sperm can be stored indefinitely.

The fertilization capacity or ability of sperm can be assessed using methods known to those of skill in the art, such as in vitro methods, including assessing the ability to fertilize the oocytes/female gamete with which they are combined/incubated (their ability to form-cell embryos, for example) and/or in vivo methods, including assessing the production of offspring by females into whom the fertilized oocytes/female gamete are implanted (mammals). Fertilization capacity or ability can be assessed using available methods, such as a functional assay, including, but not limited to, a motility assay, a viability assay, a hemizona assay (binding of the sperm to the zona pellucida) or sperm penetration into zona-free mammalian or avian oocytes.

The commercialization of cryogenically freezing avian semen has eluded scientists for decades. The freezing process has not been successful enough. Current papers cite approximately 35 to 40% semen motility after thaw. See; Comparative cryopreservation of avian spermatozoa; Benefits of non-permeating osmoprotectants and ATP on turkey and crane sperm cryosurvival. By Juan M. Blanco, Julie Long, George Gee, David E. Wildt, Ann M. Donoghue, Received 24 May 2010 Accepted 10 Dec. 2010. Elsevier B.V.

The present invention, comprising the improvement of using sap as the sole cryoprotectant, often showed greater than 50% survival based on Live/Dead stains done after the thaw of samples. Some examples showed up to 73% survival on thaw with no additional cryoprotectant being used. Once this successful idea is combined with the other currently successful ideas of science, the survival of the semen will likely be high enough to make avian semen cryopreservation a commercially viable venture.

Other animal species will likely benefit from this invention as well. There are numerous articles on scientists trying to freeze the semen of other animal species with limited success. The use of tree sap harvested at winter's first thaw, and used in cryopreservation of cell lines is an exciting and now documented success. The success of this process must also be evaluated based on the improved fertility and hatchability of eggs produced from females inseminated with frozen semen.

EXAMPLES

In general, the present invention involves the use of tree sap to cryogenically preserve avian sperm lines, preferably for use in the poultry industry, birds of prey preservation, preservation of endangered or threatened avian species, and other avian species. It will also be useful in pigs (Family—Suidae), cattle (Family—Bovidae), horses (Family—Equidae), dogs (Family—Canidae), and cats (Family—Felidae).

Table 1 contains the results of many experimental trials. In general, I obtained maple tree sap from the native trees in southeastern Wisconsin. The osmolality of Maple tree #3 is 100 mili-osmoles.

The raw dry ingredients for the preferred medium were as follows: Beltsville Turkey Extender recipe, minus the fructose; had maple tree or birch tree sap added for a final volume of 100 ml. (I added 90 ml of sap to make the final volume of the dry and wet ingredients total 100 ml.)

I began with a set of dry ingredients that was for $1/10^{th}$ of the standard recipe listed above. I added 90 ml of maple tree sap to one jar and 90 ml of birch tree sap to another jar to make a final volume of 100 ml in each jar. No other cryoprotectant was added into the mix. The fructose had been removed so the energy source for the semen came from the sucrose that was already in the sap. The cells that I am trying to preserve do not appear to metabolize fructose well and need the sucrose in the recipe to survive the freezing.

The sap was used full strength in the stock jars, but it was used in different ratios when it was added to raw semen. Sometimes a 1:1:2 dilution was used (1 part semen: 1 part BTE no fructose, plus 1/% sucrose: 2 parts BTE plus Sap); sometimes a 1:1:1 dilution was used. Sometimes a 1:1:1 dilution was used where the final mix was 33% Semen and 66% sap with sap being added into the both the base mixture and the final mixture before freezing. In all cases no other cryoprotectant was added to the sample and only the sap was used to preserve the cells in the liquid nitrogen. The cells survived in large percentages even when no additional (penetrating or non-penetrating) cryoprotectant was added to the mix.

Experiments were also done using the sap from Alaskan birch tree. Again, the raw dry ingredients for the Beltsville turkey extender, minus the fructose ($1/10^{th}$ volume of the standard recipe) had birch tree sap added for a final volume of 100 ml. [The recipe for a standard liter volume of BTE is listed above.] No other cryoprotectant was added into the mix.

The maple tree sap had been stored in 100 ml plastic bottles, with about 16 bottles per cardboard box, with the top left open. The top of the bottle had the minerals and other chemicals forced out of it leaving the ice crystals at the top. The center of the bottle had not frozen, and it remained in an almost glass like state without freezing completely after 24 hours. This type of freezing is critical to success when doing cryogenic freezing. This prevents ice crystal formation that damages the cells. [Reference; Investigation of Chemical and Physical Properties of Southwestern Wisconsin Maple Syrup; By Hiroyuki Takano, A Thesis Submitted in Partial Fulfillment of the Requirements for the Master of Science Degree with a major in Food and Nutritional Sciences. Martin G. Ondrus, Thesis Adviser; the Graduate School University of Wisconsin-Stout, Dec. 2005]

The sap of the birch tree was obtained from Alaska through a syrup company called Alaska Wild Harvest LLC, dba Kahiltna Birchworks, PO Box 2267, Palmer, Ak. 99645. I obtained both the first run and second run saps for experimentation. This sap contains three times less sugar on average, than Maple tree sap. This tree comes from higher latitudes that are subject to more severe temperatures and temperature swings than the forest in Wisconsin are. The birch tree sap froze very slowly in the chest freezer and in a similar manner to that of the maple tree sap listed in the previous paragraph.

The first semen sample that I froze was from a male Northern goshawk (*Accipiter gentilis*) using an extender recipe that was modified to include maple tree sap. This recipe consisted of all of the dry ingredients of the Beltsville Turkey Extender in the usual percentages, without the fructose. 90 ml of maple tree sap was added for a final volume of 100 ml. (This is $1/10^{th}$ of a standard recipe for BTE) One hundred percent of the liquid added into the recipe was maple tree sap. The sucrose content of the maple tree sap is reported in the literature to be between 2%-2.6%. The exact sucrose level of this sap was not measured but estimated to be about 2% because this was a first run sap. The needed minimum sugar level for the Beltsville Turkey Extender is 0.5%. So this recipe ended up having more sugar in it (than the commercial extender) because the sap had 4-5 times the needed sugar level, naturally in its sap.

This first recipe contained 4-5 times the needed sugar, making it hyperosmolar so that the sperm would gradually lose motility at room temperature. However, a frozen semen sample (Sample #69, Table 1) from the Northern goshawk (*Accipiter gentilis*) was immediately flash frozen upon mixing with the extender-sap combination 1:2 (1 part semen and 2 parts Extender/Sap combination) and 58% of the cells survived the freezing and thawing process based on a live/dead stain (Eosin/Nigrosin) and visual observations. This sample was thawed in a cool water bath at approximately 55° F. after being in the liquid nitrogen can for over a day. These cells then went on to lose motility at nearly at exactly the same rate as a sample that had been mixed and held at room temperature due to the chemical makeup of the sample. However, the cells survived the freezing process essentially unchanged. The motility and linear movement of the cells was left nearly intact, being unaltered by the freezing process. This was my first documented success and it exceeded my expectations. Cell survival post freezing showed great success.

There was no other cryoprotectant put into the sample. This recipe is clearly hyperosmolar (and detrimental to the cells) because it contained at least 2% sucrose and the sperm only needed 0.5% sucrose.

I found 58% survival upon thaw based on a live/dead Eosin/Nigrosin stain on this first sample. A hundred cells were counted using a standard lab cell counter and this simple percentage established. This exceeded literature references of 25% with standard cryoprotectants such as DMA and MA. A survival rate of above 25%, preferable above 40% or 50%, indicates a successful experiment.

A second sample of 22 ul semen (sample #81, Table 1) was then frozen. 22 ul Beltsville Turkey Extender, no fructose, plus 0.5% sucrose was added to the semen in a 0.5 ml Eppendorf tube and placed in the fridge. 44 ul of BTE with maple tree sap; was placed in its separate tube, also in the fridge at 42° F. The two liquids were combined after acclimating in the fridge for 10 minutes. The total volume was 88 ul. The sample was packaged in 2-75 ul Mylar coated capillary tubes, placed in poultry straws, this was then placed in a ventilated soda straws, and flash frozen. Both straws were thaw in a 55° F. water bath. Two straws were produced from one semen sample. Sample 1 had 25-30% live forwardly motile sperm with normal speed of travel and a live/dead stain of 50 live/50 dead. The second straw had 55% forwardly motile with normal motility and a live/dead stain of 57 live/43 dead. The semen survival increased when the percentage of the Maple sap was lowered to 50%.

Additional samples of semen from this male goshawk were frozen. The results are listed in Table 1, a table disclosing semen samples where either maple sap or birch sap were used exclusively for cryopreservation. The semen of the Northern goshawk (*Accipiter gentilis*) was used in all experiments.

I list samples in Table 1 that are successful and those that are not in the column marked "Is this sample workable?" Samples were listed as Yes, No, and Maybe. There is a column that lists the success or lack of success; so it is easy to review the table quickly by looking down this single column. I had success freezing samples in $LN_2$ as soon as I started to add the natural Maple tree sap into the formula. Semen cells survived cryogenic freezing when only tree sap was used as the cryoprotectant, even when there was no other chemical cryoprotectant used. My samples survived the trauma of freezing almost as if they had never been frozen; continuing to swim at a normal speed in a straight direction. The cells eventually lost motility due to problems associated with the solution that they were put in.

It is of particular note that some of the samples survived with even higher survival percentages and motility without the addition of other cryoprotectants, where only the sap was used. Sample 84 survived the best and is nearing the noted highest percentage of survival and motility known to scientists that work in this field of cryopreservation at 73L/27D % live/dead stain and a second sample with a 64L/36D % live/dead stain. Samples 67, 69, 70, 71, 72, 80, 81, 84, 93, 97, 118, 120, 126, and 128 show very encouraging results with progressive forward motility and the live dead stain percentages listed in the chart above. Other samples also showing this trend are also listed in the table below.

| Percentage Survival on Live/Dead Stain | Sample numbers in Table 1 |
| --- | --- |
| 0-4% Survival | 106, 113, 116, 117 |
| 5-9% Survival | 82, 100, 101, 105, 109, 110, 115, 116 |
| 10-14% Survival | 82, 88, 95, 105, 107, 110, 111, 111, 113, 114 |
| 15-19% Survival | 87, 88, 93, 100, 107, 108, 109, 115 |
| 20-24% Survival | 82, 91, 100, 102, 103, 106, 108 |
| 25-29% Survival | 99, 99, 114, 116, 117 |
| 30-34% Survival | 72, 77, 83, 89, 90, 90, 102, 109, 109, 119, 119 |
| 35-39% Survival | 44, 77, 77, 85, 91, 92, 99, 111 |
| 40-44% Survival | 68, 85, 80 |
| 45-49% Survival | 72, 83, 118 |
| 50-54% Survival | 81, 97, 103, 105, 107, 110, 112 |
| 55-59% Survival | 69, 80, 81, 93, 93, 128 |
| 60-64% Survival | 84, 120 |
| 65-69% Survival | 72, 76 |
| 70-74% Survival | 84 |

Some of the samples showed quiescense features and according to a live/dead stain, survived the freezing but were not motile. Live cells do not take up Live/Dead stain and show up as white on microscope slides, even when no longer motile. These samples are likely not dead and can be "resurrected" and made motile with known techniques. Many of the samples had cells with near normal gross cellular features post freezing and did not appear to be distorted or damaged from the freezing process; on the live/dead stains. These stains have been retained for future reference.

The sap is the key ingredient for cryopreservation because it is non-toxic, has no contagious agents to transmit to the sperm, is plentiful, has key cryo-preservative properties, is in a liquid state naturally, can be collected without bacterial contamination, and it is not viscous (thick) so it does not impair spermatic motility through the fluid medium. It is a natural product that is very unlikely to contain adulterant chemicals.

I envision typical optimizations of the present invention. First, the optimized-liquid base that supports the cell lines needing to be preserved will need to be developed and then modified to allow the addition of the sap to the mix in various percentages, so that the sap does not add chemicals in concentrations that would then kill the cells, but would still allow for cryo-protection. (For example, the osmolality of maple sap that I obtained was 100 mili-osmoles.) This osmolality appeared to be too high when it was added directly to Beltsville Turkey Recipe dry ingredients that did not have the fructose added into the recipe. The cells survived the freezing in great shape, but lost motility possibly due to the hyperosmolality of the approximately 2% sucrose in the maple sap.)

Second, the sap ingredient may be optimized just by choosing different species of trees to use. The sugar content in the saps varies with the tree species and so do the other chemicals that act as natural cryoprotectants that are not sugars. Syrup producers use maple trees that produce the most sugar and some syrup producers use birch trees for this process. They know that where maple tree sap is boiled down, between 20-50 units per one unit of syrup is required. When birch tree sap is boiled down, 150 units per 1 unit of syrup is required. Syrup producers do not tend to use maple tree species that produce low sugar content in their sap. Yet, these trees also survive the rigorous temperatures and temperature extremes and must be adapted well to survive without sugar as a main cryoprotectant, implying that other chemicals in the sap that are not sugars, are acting in this manner.

Additionally, one might wish to use a combination of saps. Combinations of the maple and birch sap recipes were used in experimentation listed in Table 1. High success rates were achieved with this combination.

Additionally, sap taken at different times during the tapping process may yield some beneficial results. Later run saps are lower in the sugars seen in the earlier run, while the trees are still going through and surviving extreme low temperature stresses. The osmolality of the saps taken at different times may be of benefit.

Additionally, extracts of the saps may yield benefits through the discovery of newly discovered antifreeze proteins or compounds that would be of use with this process. [Reference; When plant cells can survive ultra-low temperatures; Pawl M. Pukacki, Physiology of Abiotic Stress Laboratory, Institute of Dendrology, Polish Academy of Sciences, Kornik, Poland].

By "sap," we mean to include any concentration or dilution of tree sap. For example, the cryoprotectants in the sap can be concentrated. One preferable way of concentrating the sap is via reverse osmosis. This is a mechanism whereby the water is removed from the sap and the chemicals are concentrated on one side of a semipermeable membrane without having to apply heat to the sap that would likely destroy the chemicals that are cryoprotective.

Suitable Extender Recipes for 2015 and Semen Survival Study.

Number 1 Recipe;

Beltsville Turkey Extender, No fructose plus 90 ml Maple Tree sap, from first run tapping, QS to 100 ml. Dated on bottle Mar. 11, 2015, mixed on Mar. 27, 2015, Initial pH listed as 7.5 and then after being mixed the pH was 6.73 with my meter.

Maple tree sap is 2-2.6% sucrose which is 4-5 times too high and hyperosmolar. BTE normally has 0.5% Fructose in it. However goshawk eggs do not do well with Fructose and must have Sucrose to survive.

Number 2 Recipe;

Beltsville Turkey Extender, No fructose plus 90 ml Birch tree sap from Alaska, first run sap, QS to 100 ml. dated on bottle Mar. 11, 2015 and mixed on Apr. 11, 2015. Initial pH listed as 7.5 and then after mixing read on my meter as 7.62.

Number 3 Recipe;

Beltsville Turkey Extender, No fructose plus 0.5% sucrose, plus 16% Methyl Acetamide by weight. The pH was 7.78. Plus 0.2 mg Inositol (should have been 0.02 mg Inositol). It had a total volume of about 10 ml.

Number 4 Recipe;

Beltsville Turkey Extender, No fructose, plus ½% sucrose. The final pH was 7.36. The water was boiled and probably has a low oxygen tension.

Purdy formulas were a simple addition of maple tree sap, by volume to BTE. The osmolalities were as listed.

BTE, Control, No sap added, 352 mOsm
BTE, 5% Maple tree sap, 339 mOsm
BTE, 10% Maple tree sap, 326 mOsm
BTE, 20% Maple tree sap, 308 mOsm The osmolality of the 20% Maple tree sap was too low to support the cells due to cell swelling.

TABLE 1

| Number | Date Semen was Used | Date Semen was collected. | Sire donating. | Hen receiving semen. | Ratio of Semen:Extender. | Is this sample workable? | Glucose Level in mg/dl | Comments on Semen Survival and Storage. |
|---|---|---|---|---|---|---|---|---|
| 4 | Mar. 31, 2014 | Apr. 6, 2011 | Squirt | Juniper | 1 to 2 | NO | | Less than 1% motile on thaw. Most were dead. |
| 5 | Apr. 11, 2013 | Apr. 9, 2011 | Squirt | None | 1 to 3 | NO | | Large sample 40-50 ul. |
| 6 | Mar. 25, 2014 | Apr. 21, 2011 | Squirt | None | 1 to 2 | NO | | Some urate contamination. 0% motility on thaw. |
| 7 | X | Apr. 23, 2011 | Squirt | None | 1 to 2 | NO | 520 mg/dl | Small amount of urate contamination. 0% motility when thawed. On the blood glucose meter it had a 520 mg/dl reading. Impression; There was decreased speed of motility prefreezing. Was the diluent either too thick? |
| 8 | Apr. 11, 2013 | Apr. 11, 2011 | Squirt | None | 1 to 2 | NO | | There was a 2 minutes mix time and it went straight to the tank and was immersed. It was thawed on Apr. 11, 2013 and there was 0% motility |
| 9 | X | Apr. 15, 2011 | Squirt | None | 1 to 4 | NO | 435 mg/dl | Rare motility upon thaw. Less than 1%. |
| 10 | Apr. 11, 2013 | Apr. 16, 2011 | Squirt | None | 1 to 4 | NO | | Heavy urate contamination so I diluted with extender so the semen survives. O % motility on thaw. |
| 11 | Mar. 31, 2014 | Apr. 16, 2011 | Squirt | None | 1 to 1 | NO | | 0% motility on thaw. |
| 12 | Apr. 11, 2013 | Apr. 24, 2011 | Squirt | None | 1 to 2 | NO | | 2 cells seen moving. Almost no survivorship |
| 13 | Mar. 31, 2014 | Apr. 25, 2011 | Squirt | None | 1 to 2 | NO | | 0% motility on thaw. |
| 14 | Mar. 24, 2013 | Apr. 26, 2011 | Squirt | Juniper | 1 to 2 | NO | | 0% motility on thaw. |
| 15 | Mar. 24, 2013 | Apr. 26, 2011 | Squirt | None | 1 to 0 | NO | | 2% Motile questionable with thawing. |
| 16 | Mar. 31, 2014 | Apr. 27, 2011 | Squirt | None | 1 to 2 | NO | BG 5 mg/dl, retested as 66 mg/dl | 0% motility on thaw. |
| 17 | Mar. 24, 2014 | Apr. 29, 2011 | Jasper | None | 1 to 2 | NO | | Dies quickly when viewed as a wet prep w/o freezing. 0% motility upon thawing. |
| 18 | Mar. 26, 2014 | Apr. 25, 2011 | Squirt | Juniper | Unknown | NO | | 1-5% Motility on thaw. Tail agglutination a problem. Survives 3-4 hours at room |
| 19 | Mar. 25, 2014 | Apr. 30, 2011 | Squirt | Juniper | 1 to 2 | NO | | |

TABLE 1-continued

| | | | | | |
|---|---|---|---|---|---|
| 20 | Mar. 25, 2014 | Squirt | None | 1 to 3 | NO | temperatures. Viewed as a good sized sample wet prep prior to freezing.; Upon thawing saw 5% or less moving and est 1% forward motility. Then put this in Juniper. |
| 21 | May 1, 2011 | Squirt | None | 1 to 3 | NO | Viewed prior to freezing, tail agglutination is a problem, there is decreased survivorship after the extender is frozen in the fridge and used after thawing. Dilution also not 1 to 2. Viewed as a trace sample wet prep. Exploded on thaw. Capillary tube found and trace saw 0% motility. |
| 22 | May 3, 2011 | Squirt | None | 1 to 2 | NO | Good survivorship in diluent w/o freezing. Survived 1:30 PM to 6:50 PM, some survival at room temperature. When thawed after freezing there was 0% survival. |
| 23 | Apr. 11, 2013 | Squirt | None | 1 to 3 | NO | Some urate contamination. 0% motility on thaw. |
| 24 | Mar. 30, 2014 | Squirt | Juniper | 1 to 2 | YES | I put this in Juniper at 1 PM. 25% survivorship with good motility upon thawing. A lot of autoagglutination. Extender frozen prior to use in the freezer. Some survival at room temperature 1 PM to 6:50 PM with little forward motility in wet prep. Impressions: Trout #1 seemed better; Extender best used fresh and not frozen; Cells died faster on this slide and there was more agglutination-Stored extender in 5 cc vials and it was colder at time of use. (Important = Cold shock.) |
| 25 | Apr. 2, 2014 | Squirt | Juniper | 2 to 5 | MAYBE | Heavy urate contamination. On thaw there was less than 5% |

TABLE 1-continued

| | | | | | |
|---|---|---|---|---|---|
| 25 | Jun. 13, 2013 | Squirt | None | | motility due to trauma from the explosion of liquid nitrogen. Kevin retrieved this from the can. Used in Juniper the day the tank was filled. |
| 26 | Apr. 11, 2013 | Squirt | None | 1 to 4 | NO | Minor urate contamination, 1% good forward motility with a Ice water thaw. |
| 27 | Jun. 2, 2013 | Squirt | None | 1 to 3 | NO | Minor urate contamination, 0% forward motility on Ice water thaw. |
| 28 | Jun. 3, 2013 | Squirt | None | 1 to 8 | NO | 0% motility on cold water thaw. No cryoprotectant used. |
| | | | | 1 to 4 | NO | Lost most of the sample. Unable to evaluate. No survival seen in ones diluted with water. Cold water thaw. |
| 29 | Mar. 31, 2014 | Squirt | Juniper | 1 to 3 | NO | Less tail agglutination with this formula. More rapid cell death though after only 20 minutes. Maybe 30% survival, 5% forward motility at 1 hour. None alive on wet prep at 6:50 PM, (collected 1 PM), impression, sperm dies fast in this extender. Less than 1% motile on thaw and put in Juniper Mar. 31, 2014. |
| 30 | Apr. 14, 2013 | Squirt | Juniper | 1 to 2 | NO | No motility seen on fresh wet prep. 7 very mobile cells seen, 1 cell was moving fast and then slowed down and stopped. I used Trout #2 plus ¼ tsp Sorbitol and ⅛ tsp Arabogalactin. |
| 31 | Mar. 30, 2014 | Squirt | Juniper | 1 to 4 | MAYBE | Trace sample after exploding saw some motility |
| 32 | X 2014 | Squirt | Juniper | 16% | NO | 8 mm of Semen placed in room temperature Turkey Extender went to the fridge for 30 minutes acclimation time, Added 3 units DMA for a final volume of 50 mm. Quickly placed over liquid nitrogen in under 60 seconds. |

TABLE 1-continued

| | | | | | |
|---|---|---|---|---|---|
| 33 | X 2014 | Squirt | Juniper | 44% | NO | 22 mm of Semen was placed in Turkey Extender at room temperature and placed in the fridge and acclimated for 30 minutes. 3 units/ul of DMA was added. I was placed over the liquid nitrogen in under 60 seconds. It was hung over the vapors for 10 minutes and then flash frozen. |
| 34 | Jun. 1, 2013 | Squirt | Juniper | 48% | NO | 24 mm of Semen was placed in Turkey Extender at room temperature to a volume of 47 mm and then acclimated in the fridge for 30 minutes. 3 ul of DMA was added quickly and then the sample was hung over the vapor (in less than 60 seconds) for 10 minutes and then immersed in liquid nitrogen. |
| 35 | Jun. 2, 2013 | Squirt | Juniper | 20% | NO | 8-10 mm of Semen was collected and Turkey Extender was added that was at fridge temperatures. The final volume with DMA was 50 ul/mm. 35 mm of Extender and 5 ul of DMA was used to make it 10% DMA. "No motility" (probably too cold) seen on the smear on the fresh wet prep. When thawed on ice water 5-10% were seen moving. Only 1% with good not great forward motility. There was progressive loss of motility over minutes. (45 minutes). This is the likely sample that went into Juniper on 4/3. |
| 36 | Apr. 3, 2014 | Squirt | Juniper | 8% | | 4 mm of Semen was collected and Turkey Extender that was refrigerator temperature was added to a volume of 47 mm. This was left in the |

TABLE 1-continued

| | | | | | |
|---|---|---|---|---|---|
| | | | | | fridge at 40 F. from 7 AM to 6:30 PM. 3 ul of DMA was added quickly and in less than a minute it was hung over the vapors for 10 minutes and then immersed. 50% great motility off trace sample seen before adding the DMA. |
| 37 | Mar. 26, 2014 | Squirt | None | 8% | 4 mm of Semen was collected and Turkey Extender was added to a volume of 45 mm. It was acclimated for 30 minutes and then 5 ul (10%) DMA was added. It was Flash Frozen. |
| 38 | Mar. 26, 2014 | Squirt | None | 8% | 2 mm of Semen was collected and Turkey Extender 23 mm was added and it was acclimated in the fridge for 30 minutes. (10%) DMA was added quickly and it was Flash Frozen in under a minute. |
| 39 | Mar. 26, 2014 | Squirt | None | 8% | 4 mm of Semen was collected and 45 mm of Turkey Extender was added and it was acclimated in the fridge for 30 minutes. 5 ul of DMA was added (10%) and it was Flash Frozen after mixing in under a minute. |
| 40 | Mar. 26, 2014 | Squirt | None | 4% | 1 mm of Semen was collected and 8 mm of Turkey Extender was added and it was acclimated in the fridge for 30 minutes. 2 ul of DMA was added and it was flash frozen after mixing in under a minute. |
| 41 | 2013 4 SAMPLES FLOATING IN THE LIQUID NITOGEN. | Squirt | Juniper | YES | 4 TUBES THAT WERE PRESERVED IN 2013 THAT WERE PUT IN COMMERCIAL PLASTIC TUBES WITH BEADS TO CAP THE ENDS. SEMEN WAS IN CAPPILLARY TUBES, WERE FOUND |

TABLE 1-continued

| | | | | |
|---|---|---|---|---|
| 42 | May 2, 2014 | Squirt | 3 mm Semen to 30 units of Turkey extender, plus 1.5 units DMA | FLOATING IN THE LIQUID NITROGEN ON TOP, BUT LOST THEIR LABELS. SOME OF THESE SAMPLES CONTAINED 25% SURVIVAL OF SEMEN SAMPLES AND WERE ACTIVELY MOVING FORWARD. THESE WERE PUT INTO JUNIPER. ONE OF THE RED AND FOUR OF THE GREEN SAMPLES APPEAR TO BE WHAT I USED FOR AI IN JUNIPER. I DO NOT KNOW WHICH TUBE WAS WHICH BUT I DO KNOW THAT I LOST 3 RED SAMPLES ON THAW DUE TO EXPLODING. THE REMAINING SAMPLES DID NOT LEAK IN THE PRIMARY CONTAINER. MOST OF THE GREEN SAMPLES WERE NOT LOST. THE ENTIRE TANK WAS EMPTIED OF ALL OF ITS SAMPLES IN 2014, STARTING OVER. 16 SAMPLES FOR 2013 PUT IN THE TANK. No urates. Low cellularity. |
| 43 | May 1, 2014 | Squirt | 6 mm Semen, diluted to 30 mm volume, added 1.5 units DMA | Some urate contamination. Low cellularity. |
| 44 | Mar. 1, 2016 | Squirt | | NO | No urates. Low cellularity. Mar. 1, 2016 Thawed in an ice water bath. Low cellularity due to males age. Less than 10% |

TABLE 1-continued

| | | | | |
|---|---|---|---|---|
| 45 | Mar. 29, 2015 | | | motile. Can not do a Live/Dead stain as cellularity is too low. |
| | | Squirt | 2 mm of Semen plus 18 mm of Turkey extender to a total volume of 20 mm. | NO No urates. Low cellularity. Goshawk semen requires sucrose and not fructose to survive freezing!!! This is why these cells survived in the Trout Extender #2 and not the Turkey Extender that has the Fructose! You must use Beltsville Turkey Extender minus the Fructose, with sucrose added back in to .5% (½%) |
| 46 | May 4, 2014 | Squirt | 6 mm of Semen, plus 19 mm of Turkey Extender, plus 2 ul of DMA. | Low number of urates. Low cellularity. |
| 47 | May 5, 2014 | Squirt | 1-40 mm sample contaminated with urates split into 2-20 mm samples, plus 28 mm Turkey extender, plus 3 ul of DMA (6%). | 1 side of the split sample had more urates than the other, semen in only one spot on the tube, so separated into ½ to put most urates in 1 tube. Low cellularity. |
| 48 | May 6, 2014 | Squirt | 6 mm of Semen, plus 14 mm of Turkey extender to a total volume of 20 mm. Plus 1.5 ul of DMA, (7%) | No urates. Low cellularity. |
| 49 | May 6, 2014 | Squirt | 10-16 mm of Semen | Many urates. Small amount of semen in one |

TABLE 1-continued

| | | | | |
|---|---|---|---|---|
| 50 | May 7, 2014 | Squirt | plus 47 mm of Turkey extender, plus 3 ul of DMA. | spot. Final volume 50 mm. Low cellularity. |
| | | | 6 mm of semen plus 19 mm of Turkey extender plus 2 ul of DMA. | No urates. Low cellularity. |
| 51 | May 7, 2014 | Squirt | 6 mm of Semen plus 19 mm of Turkey extender plus 1.25 ul of DMA (5%). | No urates. Low cellularity. Lots of blast cells seen. Goshawk semen requires sucrose and not fructose to survive freezing!!! This is why these cells survived in the Trout Extender #2 and not the Turkey Extender that has the Fructose! You must use Beltsville Turkey Extender minus the Fructose, with sucrose added back in to .5% (½%) |
| 52 | Mar. 29, 2015 | None | | NO |
| | May 9, 2014 | Squirt | 5 plus mm of Semen and about 8 mm of Urates, plus 27 mm of Turkey extender to a total volume of 40 mm plus 2.7 ul of DMA (6%) | Watery urates seen in 8 of 13 mm total initial semen volume so had about 5 mm of semen present. Low cellularity. Goshawk semen requires sucrose and not fructose to survive!! These cells can not use fructose and this is why these cells survive in the Trout #2 extender! |
| 53 | May 10, 2014 | Squirt | 16 mm of Semen plus 22 mm of Turkey extender for a final volume of 38 mm, plus 2.23 ul of DMA, (6%). | No urates and cellularity is low but going up. |
| 54 | May 22, 2014 | Squirt | 5 mm of Semen plus 15 mm | No urates and cellularity is low but going up. |

TABLE 1-continued

| | | | | | |
|---|---|---|---|---|---|
| 55 | May 12, 2014 | Squirt | of Turkey extender to a final volume of 2 mm, plus 1 ul of DMA (5%). 14 mm of Semen plus 23 mm Turkey extender to a total of 47 mm. Plus 2.5 ul of DMA (5%). | | A few urates, but not a lot. Low cellularity but increasing. |
| 56 | May 13, 2014 | Squirt | 4 mm of Semen plus 20 mm of Turkey extender plus 5% Maple Syrup, plus 1 ul DMA (5%). | Unknown, meter could not read this number. | No |
| | May 14, 2014 | | | | No urates. Cellularity is low but climbing. Storage straw did not leak and the cell survivorship was feeble. |
| 57 | Apr. 4, 2015 | Odin | 8 mm of Semen plus 11 ul of Beltsville Turkey Extender (unaltered) Plus 1 ul of DMA. Total volume 20 ul. | No | No semen survived freezing. The fructose in the sample is the suspected problem because it slows the speed of the spermatozoa down by half in fresh samples extended with this TE. The cryoprotectant needs to also be looked at. All 2015 samples placed in cold Eppendorf tubes that were already in the fridge. Temperature shock might be present. Might be too cold next to refrigerator coils. Goshawk semen requires sucrose and not fructose to survive freezing!!! This is why these cells survived in the Trout Extender #2 and not the Turkey Extender that has the Fructose! You must use Beltsville Turkey Extender minus the |

TABLE 1-continued

| | | | | | |
|---|---|---|---|---|---|
| 58 | Apr. 18, 2015 | Mar. 23, 2015 | Odin | None | 30 ul of Semen plus 30 ul of Turkey extender plus Inositol. Plus 2.6 ul of DMA, 62.6 ul total volume. | NO | Fructose, with sucrose added back in to .5% (½%) All 2015 samples placed in cold Eppendorf tubes that were already in the fridge. Temperature shock might be present. Might be too cold next to refrigerator coils. Lost sample across the garage as it exploded. |
| 59 | Apr. 18, 2015 | Mar. 23, 2015 | Odin | None | 30 ul of Semen plus 30 ul of Turkey extender plus Inositol. Plus 2.6 ul of DMA. 62.6 ul total volume. So this is 4% DMA. | NO | A sample that was still left in the tube before freezing had 25% survival based on a live/dead stain. All 2015 samples placed in cold Eppendorf tubes that were already in the fridge. Temperature shock might be present. Might be too cold next to refrigerator coils. Less than 1% Motile with 55 F. water bath and hand warming. |
| 60 | Apr. 18, 2015 | Mar. 25, 2015 | Odin | None | 12 ul of Semen plus 24 ul of Turkey Extender plus Inositol. Plus 2 ul of DMA. 38 ul total volume. So this is 5% DMA | NO | All 2015 samples placed in cold Eppendorf tubes that were already in the fridge. Temperature shock might be present. Might be too cold next to refrigerator coils. No survival on thawing. Thawed in a cool water bath at 55 F. and hand warming. |
| 61 | Apr. 18, 2015 | Mar. 25, 2015 | Odin | None | 10 ul of semen plus 18 ul of Turkey extender plus Inositol, plus 2 ul of DMA To a total volume of 30 ul. 6.6% DMA | NO | All 2015 samples placed in cold Eppendorf tubes that were already in the fridge. Temperature shock might be present. Might be too cold next to refrigerator coils. Thawed in cool water bath at 55 F. and hand warming. No cell survival. |

TABLE 1-continued

| | | | | | | |
|---|---|---|---|---|---|---|
| 62 | Apr. 15, 2015 | Mar. 27, 2015 | Odin | None | 15 ul of Semen plus 30 ul of Beltsville Turkey Extender plus Inositol, plus 2 ul of DMA, or 4.25% DMA | NO | All 2015 samples placed in cold Eppendorf tubes that were already in the fridge. Temperature shock might be present. Might be too cold next to refrigerator coils. Thawed in cool water bath at 55 F. and then put on a warming plate. Less than 1% survival. |
| 63 | Apr. 15, 2015 | Mar. 27, 2015 | Odin | None | 20 ul of Semen plus 37 ul of Beltsville Turkey Extender plus Inositol, plus 3 ul of DMA, 5% DMA | NO | All 2015 samples placed in cold Eppendorf tubes that were already in the fridge. Temperature shock might be present. Might be too cold next to refrigerator coils. Thawed in a cool water bath at 55 F. No cells survived. |
| 64 | Apr. 15, 2015 | Mar. 28, 2015 | Odin | None | 16 ul of Semen plus 29 ul of Beltsville Turkey Extender with Inositol, plus 3 ul of DMA, 6.25% DMA | NO | All 2015 samples placed in cold Eppendorf tubes that were already in the fridge. Temperature shock might be present. Might be too cold next to refrigerator coils. Thawed in a cool water bath at 55 F. No cells survived. |
| 65 | Apr. 15, 2015 | Mar. 28, 2015 | Odin | None | 14 ul of Semen in 16 ul of Beltsville Turkey Extender plus Inositol, plus 2 ul of DMA, 6.25% DMA | NO | All 2015 samples placed in cold Eppendorf tubes that were already in the fridge. Temperature shock might be present. Might be too cold next to refrigerator coils. Thawed in a cool water bath at 55 F. and then put on a warming plate. No cells survived. |
| 66 | Apr. 15, 2015 | Mar. 28, 2015 | Odin | None | 13 ul of Semen in 20 ul of Beltsville | NO | All 2015 samples placed in cold Eppendorf tubes that were already in the fridge. Temperature shock might |

TABLE 1-continued

| | | | | | |
|---|---|---|---|---|---|
| 67 | Mar. 30, 2015 | | | | Turkey Extender plus Inositol, plus 2 ul of DMA, 5.7% DMA. | |
| | Mar. 29, 2015 | Odin | None | 16 ul of Semen plus 24 ul of BTE, no fructose, plus Maple tree sap, no other cryoprotectant | MAYBE | 5 times higher than BTE normally is so this is hyperosmolar. | be present. Might be too cold next to refrigerator coils.

This sample was flash frozen with no acclimation. When I thawed it, it took off living just like the sample did that was viewed at room temperature. There was about 11% motility and less than half of these were moving forward well on thaw. A sample that was left on a slide at room temperature had the mature spermatids stop moving within 5 minutes but the immature spermatids did well and kept on moving. The speed of movement was much better and this is clearly an improvement over the BTE with fructose. I can assume that goshawk semen needs sucrose to survive. The sap is 100 milliosmoles and was added to the dry ingredients of the BTE, no fructose. This added in sucrose at 5 times the percentage needed and made it hyperosmolar. The caused the mature cells to die. The immature spermatids, with immature cell walls, could equalize the osmotic pressure. Maple sap is .5-2.6% sucrose. This is first run sap so it is higher in sucrose than last run. Different maple tree species have different percentages of sucrose.

TABLE 1-continued

| | | | | | | |
|---|---|---|---|---|---|---|
| 68 | Apr. 15, 2015 | Odin | None | ? | NO | | 6% DMA, No survival |
| 69 | Mar. 31, 2015 | Odin | None | 19 ul of Semen plus 38 ul of BTE plus Maple tree sap, first run, tree number 3, No other cryoprotectant | MAYBE, MORE SUCCESS THAN I HAD HOPED FOR. | Sucrose likely 5 times what is needed, so this sample is hyperosmolar. | Most of the sample was lost on thaw. The trace in the sample has 66% motility based on visual estimates. 25 out of 43 alive on a swim count with the counter. On a live dead stain there was Live 58/42 Dead! |
| 70 | Apr. 15, 2015 | Odin | None | 25 ul of Semen, plus BTE, no fructose, plus 50 ul of Maple tree sap, No other cryoprotectant. | YES, but can do better. | Sucrose likely 5 times what is needed, so this sample is hyperosmolar. | This tube is completely full. 5-10% motility on thaw with normal motility. Thawed in 55 F. water bath and then placed on a warm plate. |
| 71 | Apr. 15, 2015 | Odin | None | 16 ul of Semen plus BTE, no fructose, plus 28 ul of Maple tree sap, No other cryoprotectant. | YES | Sucrose likely 5 times what is needed, so this sample is hyperosmolar. | Thawed in 55 F. water bath and then placed on a warming plate. 10% motility at thaw and then the cells slow their motility to 5% estimated visually over 5 minutes. |
| 72 | Apr. 4, 2015 | Odin | None | 13 ul of Semen plus BTE, no fructose, plus 26 ul of Maple Tree sap, no other cryoprotectant was used. | YES | Sucrose likely 5 times what is needed, so this sample is hyperosmolar. | Thawed in a 55 F. water bath and then a warming plate. 20% near normal motility and motility estimated visually. Thawed fast! Ventilated soda straw is key. |
| 73 | Apr. 12, 2015 | Odin | None | 20 ul of Semen plus 40 ul of BIRCH tree sap | NO | Sucrose level reads at 479 mg/dl on a Accucheck glucose meter. | At room temperature, cells slow rapidly on a wet prep, probably still too hyperosmolar. No motility on thaw with 55 F. water bath and then a warming plate. |
| 74 | Apr. 12, 2015 | Odin | NONE | 42 ul of Semen, plus BTE, no fructose, plus | MAYBE | | Apr. 14 2015 Sample #1 Orange straw; Thawed in cold water and then placed on a warming plate. 5-10% motility of |

TABLE 1-continued

| | | | | | |
|---|---|---|---|---|---|
| 75 | Apr. 13, 2015 | Odin | | Sucrose, Added in 75 ul of BTE, minus fructose, plus sucrose ½% plus MA (methyacetamide) 45 ul of Semen split between 3 straws, BTE no fructose, plus ½% sucrose, plus 84 ul of BTE (same as above) with MA (Methyacetamide) | normal looking sperm. The rest are moving a little but not swimming forward. |
| 76 | Feb. 28, 2016 | Odin | None | 7 ul of Semen with 26 ul of BTE, no fructose, plus ½% sucrose. Plus 2 ul of DMA cryoprotectant. Final volume of 35 ul. | Yes | Sample was prepped at room temperature with all items starting at 70 F. Feb. 28, 2016 Teal Blue Straw, Not ventilated, 80% of cells vibrating, 10% moving actively, Thawed in a 41 F. water bath. Live 65/45 Dead Stain. |
| 77 | Feb. 28, 2016, Mar. 1, 2016 | Odin | None | 55 ul of Semen plus 110 ul of BTE, no fructose, plus ½% sucrose, chilled in the fridge for 10 minutes, plus 8 ul of DMA | This is one of the first samples of NO FRUCTOSE plus DMA to test if it is the fructose or DMA that is causing the samples to fail. | All materials start at room temperature (70 F.) and then go to fridge to chill to 41 F. Cold packs were used to carry to the garage. Feb. 28, 2016 Thawed in 41 F. water bath to a warming plate with Live 39/61 Dead. Mar. 1, 2016 Thawed in a 41 F. water bath to a warming plate with 10% swimming normally and 50% vibrating in place. |

TABLE 1-continued

| | | | | |
|---|---|---|---|---|
| 78 | Apr. 18, 2015, Apr. 18, 2015 | Apr. 15, 2015 | Odin | None | 38 ul of Semen, plus 75 ul of Birch Sap, BTE, no fructose, first run.. | Feb. 28, 2016 Yes, No movement-green tube, Thawed 41 F. water bath. Little cell deformity with a Live 39/61 Dead stain. Sample quiescent. Mar. 1, 2016 Yes, 10% are swimming normally, 50% are vibrating, Thawed in a 41 F. water bath. Live 32/68 Dead stain. Maybe, because the sap preserves the semen when frozen. But the amount of sap needs to be reduced. Similar response to Maple tree sap. The cells survive the freeze | Acclimated at 41 F. in fridge with sap separate from semen until placed in capillary tubes for freezing. Acclimated for 10 minutes. Apr. 18, 2015 Thawed in a 55 F. water bath. Sample 1 showed 5% spermatozoa moving forward normally with a live/dead stain of 32/68. May 18, 2015 Sample 2 had about 5% moving forward normally with a live/dead stain of 34/66. |

TABLE 1-continued

| | | | | | |
|---|---|---|---|---|---|
| 79 | Apr. 18, 2015, Apr. 18, 2015 | Apr. 17, 2015 | Odin | None | 28 ul of Semen, plus 28 ul BTE, no fructose, plus ½% sucrose, plus 56 ul Birch Tree sap in BTE, no fructose, final volume of 112 ul with 1:3 semen to Birch tree sap extender. | but stop moving due to hyperosmolality. Maybe, because the sap preserves the semen when frozen, but the amount of sap needs to be reduced. Similar response to Maple tree sap. The cells survive the freeze but lose motility due to hyperosmolality. Maybe, Maybe | This was first run Birch tree sap from Alaska. It was acclimated after mixed by only placing it between gel packs that were at 41 F. from the fridge and then it was flash frozen. Two straws were made from this sample. One was a yellow, and the other green, ventilated soda straws. One tube had 2-5% forward moving sperm on visual estimate with a live/dead stain of 21/79. The second tube had 0% forwardly moving and no live dead stain was done. Thawed in a 55 F. cool water bath. |
| 80 | Apr. 18, 2015, Apr. 18, 2015 | Apr. 17, 2015 | Odin | None | 50 ul of Semen had 50 ul of BTE, no fructose, plus 1/% sucrose added together in 1 tube. Later 100 ul of BTE, no fructose, plus Maple sap was added for a final volume of 200 ul. Making the semen ¼ of the total mix. | | Thawed in a cool water bath of 55 F. Apr. 18, 2015 First sample 2-3% normal motility, with a live/dead stain of 57/43.; Apr. 18, 2015 The second sample had 5-10% moving forward normally and a live dead stain of 42/58. |

TABLE 1-continued

| | | | | | |
|---|---|---|---|---|---|
| 81 | Apr. 18, 2015, Apr. 18, 2015 | Apr. 18, 2015 | Odin | None | 22 ul of Semen had 22 ul of BTE, no fructose, plus ½% sucrose added to it placed in 1 tube. Later 44 ul of BTE, no fructose, plus Maple tree sap was added for a final volume of 88 ul. | YES, YES | Thawed in a cool water bath of 55 F. Apr. 18, 2015 First sample had 25-30% normal motility with a live dead stain of 50/50.; Apr. 18, 2015 The second sample had about 55% normal forward motility with a live/dead stain of 57/43. 100 cells were counted in each group. |
| 82 | May 10, 2015, Feb. 24, 2016, Green straw-Holder 5, Mar. 2, 2016 Green straw-Holder 6, Mar. 2, 2016 Green straw Holder 6. | Apr. 20, 2015 | Odin | None | 65 ul of Semen, plus 65 ul BTE minus fructose, plus ½% sucrose. Later 130 ul of BTE minus fructose plus Birch tree sap first run. | Yes, Maybe, No, No | Acclimated at 41 F. in fridge with sap separate from semen until placed in capillary tubes for freezing. Acclimated for 10 minutes. Then flash frozen. Ice water thaw, 10-15% good motility, Live Dead Stain 24 live/76 dead. Feb. 24, 2016 Thawed in a 41 F. ice water bath, 2-3% moving forward well, pH 7.0-7.2 with a Live22/78 Dead Stain. Mar. 2, 2016 Thawed in a 41 F. Ice water bath, Green Straw Holder 6, Rare motile sperm with a Live 10/90 Dead Stain. Cells are very distorted. Mar. 2, 2016 Thawed in an ice water bath at 41 F. No motility and the cells are very deformed. Live 7/93 Dead. |
| 83 | May 3, 2015, Mar. 6, 2016, Mar. 6, 2016 | Apr. 20, 2015 | Odin | None | 60 ul of Semen, plus 60 ul of BTE - fructose, + ½% sucrose. Later 60 ul | No, No Mar. 6, 2016 Yellow straw, water got into sample. YES | Acclimated at 41 F. in fridge with sap separate from semen until placed in capillary tubes for freezing. Acclimated for 10 minutes. Then flash frozen. May 3, 2016 Thawed in Ice |

TABLE 1-continued

| | | | | | |
|---|---|---|---|---|---|
| | | | of BTE plus Maple tree sap, first run Tree #3. added for a final volume of 180 ul. | Mar. 6, 2016 Yellow straw | water, 2% forward motility, Live dead stain, 39 live/61 dead. Mar. 6, 2016 Thawed in ice water at 41 F. 1% Motile and 1% moving in place. Live 33/67 Dead stain. A lot of agglutination. It was exposed to water on thaw because it lost the caulk on the end of the tube. Mar. 6, 2016 Thawed in a ice water bath. 15-20% are motile. Agglutination is present. Live 49/51 Dead. |
| 84 | May 3, 2015, Mar. 1, 2016, Mar. 6, 2016 | Odin | Apr. 21, 2015 | None | 50 ul of Semen had 50 ul of BTE, no fructose, plus 1% sucrose added together in 1 tube. Later 100 ul of BTE, no fructose, plus Maple sap was added for a final volume of 200 ul. Making the semen ¼ of the total mix. | YES, YES, YES | Acclimated at 44 F. in fridge with sap separate from semen until placed in capillary tubes for freezing. Acclimated 10 minutes. Then flash frozen. May 3, 2015 Thawed in Ice water bath, 55%-60% forward motility, Live dead stain 39/61. No pH done. Mar. 1, 2016 Thawed in an ice water bath at 41 F., Over half are moving forward with fast motility, pH of 7, with a Live 64/36 Dead stain. Mar. 6, 2016 Thawed in an ice water bath at 41 F. Over 60% are motile with little deformity. They have fast motility with a Live 73/27 Dead stain. |
| 85 | Mar. 2, 2016, Mar. 2, 2016 | Odin | Apr. 21, 2015 | None | 50 ul of Semen had 50 ul of BTE, no fructose, plus 1% sucrose added together in 1 tube. Later 50 ul of BTE, no fructose, plus Maple sap was | Maybe - Quiescent, Maybe Quiescent | Acclimated at 44 F. in fridge with sap separate from semen until placed in capillary tubes for freezing. Acclimated 10 minutes. Then flash frozen. Mar. 2, 2016 Thawed in an ice water bath and put on a warming plate. Had 5% forward motility and a Live 36/64 Dead stain. Mar. 2, 2016 Yellow straw, Thawed in an ice water bath at 41 F. Less than 1% |

TABLE 1-continued

| | | | | | |
|---|---|---|---|---|---|
| | | | | added for a final volume of 150 ul. Making the semen 1/3 of the total mix. | are motile with a Live 40/60 Dead stain. |
| 86 | May 3, 2015, May 3, 2015 | Apr. 21, 2015 | Odin | None | 10 ul of semen plus 10 ul of BTE – Fruc, + 1/2% sucrose, PLUS YOLK, Later 12 ul of BTE – Fruc, Plus Maple sap, first run tree 3. | No, Maybe | No acclimation in the fridge. Flash frozen. May 3, 2015 First sample thawed in ice water, No motility, pH of 7 on pH paper, May 3, 2015 Second sample thawed in ice water, 2-5% motility, pH 7 on paper. Live dead stain 48 live/52 dead. |
| 87 | Mar. 7, 2016 | Apr. 22, 2015 | Odin | None | 16 ul of Semen, plus 16 ul BTE – Fruc, + 1/2% sucrose, PLUS YOLK, Later 16 ul BTE – Fruc, plus Maple sap, plus 10% Yolk. Final volume 48 ul. | Maybe - Quiescent. The cells are not distorted but likely quiescent and not motile. | Acclimated in the fridge in separate tubes at 43 F. Mixed, packaged, and then flash frozen. Mar. 7, 2016 Pink soda straw 1% Motile/Cells not distorted. Live 19/81 Dead stain. |
| 88 | May 3, 2015, Mar. 2, 2016 Pink straw Holder #6, Mar. 6, 2016 Pink straw Holder #6. | Apr. 22, 2015 | Odin | None | 53 ul of Semen, plus 53 ul of BTE – fructose, + 1/2% sucrose, PLUS YOLK, Later 53 ul of BTE – fructose, + Maple sap, plus 10% YOLK | Yes, No Thawing too warm. No Cold water thaw is no better. | Acclimated in the fridge in separate tubes at 43 F. Mixed, packaged, and then flash frozen. May 3, 2015 Thawed in Ice water, 10% moving forward, pH of 7. Live dead stain, Live 38/62 Dead. Mar. 2, 2016 Thawed in a 55 F. water bath, Less than 1% motile, many cells deformed with a Live 16/84 Dead stain. Mar. 6, 2016 Thawed in an |

TABLE 1-continued

| | | | | | |
|---|---|---|---|---|---|
| 89 | May 10, 2015, Mar. 2, 2016 | Odin | None | 45 ul of Semen with 55 ul of BTE − fructose, + ½% sucrose and YOLK added in at 10%, Later 35 ul of BTE + Birch Tree Sap so that it becomes 26% Birch Tree Sap. | No, No | ice water bath, 0% motile, Cells not deformed with a Live 13/87 Dead stain. Acclimated in the fridge in separate tubes at 43 F. Mixed, packaged, and then flash frozen. May 10, 2015 A trace sample of this tube survived well at room temperature. pH of 7, Ice water bath thaw, Less than 1% motile, Live dead stain could not be done. Could not read the Live/Dead stain due to the yolk being present in the sample. Mar. 2, 2016 Orange tube, Thawed in an ice water bath, Less than 1% motile with a Live 33/67 Dead stain. Many cells are deformed. |
| 90 | May 3, 2015, Mar. 1, 2016, Mar. 2, 2016 Holder 6 Green Straw | Odin | None | 45 ul of Semen with 55 ul of BTE − fructose, + ½% sucrose and YOLK added in at 10%, Later 32 ul of BTE + Birch Tree Sap so that it becomes 19.7% Birch Tree Sap. | Maybe, Maybe appears Quiescent. Maybe appears Quiescent. | Acclimated in the fridge in separate tubes at 43 F. Mixed, packaged, and then flash frozen. May 3, 2015 Thawed in a 55 F. water bath. Less than 1% motile or no motility. Mar. 11, 2016 Thawed in a ice water bath, No motility but the cells are not deformed with a Live 34/66 Dead stain = Quiescence. Mar. 2, 2016 Thawed in a ice water bath. No motility but the cells are not deformed with a Live 31/69 Dead stain = Quiescence. |
| 91 | Feb. 24, 2016 Green soda straw from Holder #4, Feb. 24, 2016 Deep blue soda straw from Holder #4. | Odin | None | 30 ul of Semen, with 60 ul of BTE − fructose, + ½% sucrose. Later 30 ul of BTE − fructose, plus ½% sucrose | Maybe, Maybe appears Quiescent. | Mixed at room temperature and then placed between gel packs at 43 F. Then flash frozen. Feb. 24 2016 Green soda straw from Holder #4 Thawed in an ice water bath at 41 F. Cells not deformed and 2-3% motile with a Live 23/77 Dead stain. Feb. 24 2016 Deep blue |

TABLE 1-continued

| | | | | | |
|---|---|---|---|---|---|
| 92 | Feb. 28, 2016 | Odin | None | 15 ul of Semen plus 15 ul of BTE - fructose, + ½% sucrose, plus 15 ul of BTE - fructose, + ½% sucrose plus 18% MA (final of 6% MA). | plus 18% MA (diluted to a total percentage of 4.5% MA) | straw from Holder #4, Thawed in an ice water bath at 41 F., Cells not deformed 80% and 1% motile. But this tube had 10-20% deformed cells overall with a Live 35/65 Dead stain. Mixed at room temperature and then placed between gel packs at 43 F. The flash frozen. Feb. 28, 2016 Thawed in an ice water bath at 41 F., ventilated soda straw with 10% moving forward and a Live 35/65 Dead stain. Little cell distortion. |
| | | | | Maybe appears Quiescent with 10% movement. | | |
| 93 | Feb. 24 2016, Green straw Holder #4, Feb. 24, 2016 Green straw Holder #4, Feb. 24, 2016 Green straw Holder #4. | Odin | None | 45 ul of Semen, with 45 ul of BTE - fructose, + ½% sucrose, Later 45 ul of BTE - fructose + ½% sucrose plus 18% MA = 6% MA final concentration | Yes, Yes, Yes | Chilled 10 minutes at 45 F. Mixed packaged and then flash frozen. Feb. 24 2016 Green straw Holder #4 Thawed in an ice water bath at 41 F., cells not deformed with 2-3% motile. Quiescent but alive with Live 55/45 Dead stain. Feb. 24 2016 Green soda straw Holder #4 Thawed in an ice water bath at 41 F., cells not deformed, 25-30% motile and showed slowing motility over 5 minutes with a Live 57/43 Dead stain. Feb. 24 2016 Green soda straw from Holder #4. Thawed in an ice water bath at 41 F. Cells were not deformed and had 5% motile with slowing of motility over 5 minutes. The live/dead stain was hard to read but had Live18/82 Dead. |
| 94 | May 10, 2015, May 10, 2015 | Odin | None | 20 ul of Semen | No | Chilled for 10 minutes and then added DMA. Ice |

TABLE 1-continued

| | | | | | |
|---|---|---|---|---|---|
| 95 | May 3, 2015, Mar. 6, 2016 Orange straw | Odin | None | plus 55 ul of BTE - fructose, + ½% sucrose. Later 4.9 ul of DMA added. | water bath thaw. Almost no motility, No live dead stain done. Assessment; DMA is not working. |
| 96 | Apr. 26, 2015 | Odin | None | 22 ul of Semen plus 66 ul of BTE + 10% Maple Sap PURDY FORMULA. | No, Maybe | I AM STARTING THE PURDY FORMULAS THAT ARE BTE WITH DIFFERENT PERCENTAGES OF MAPLE TREE SAP IN THE DILUTION. THESE HAVE FRUCTOSE AND SUCROSE IN THEM. SEE SHEET ON THESE FORMULAS. May 3, 2016 Ice water bath thaw, 2% moving forward, pH of 7 on paper. Mar. 6, 2016 Thawed in an ice water bath at 41 F. Orange straw with 2% moving forward and 2% moving in place with a Live 14/86 Dead stain. |
| 96 | Apr. 27, 2015 | Odin | None | 18 ul of Semen with 54 ul of Purdy 10% Maple tree sap. 1:3 dilutions. | No | May 10, 2016 Ice water bath thaw, 1-3% of these moving forward. Live dead stain 31 live/69 dead. Comments; Fructose, No acclimation, and high pH might be a problem. |
| 97 | Mar. 6, 2016 Pink soda straw Holder #6 | Odin | None | 12 ul of Semen plus 36 ul of Purdy 10 % Maple Tree sap. | YES! | Mar. 6, 2016 No acclimation and was thawed in an ice water bath. Greater than 50% moving, with 20% moving normally. There was a Live 52/48 Dead stain. |
| 98 | | | Purdy Formulas | Purdy formulas begin with #95 | | Purdy formulas begin with #95. |
| 99 | Feb. 24, 2016 Holder #5 Pink soda straw, Feb. 24, 2016 | Odin | None | 50 ul of Semen with 100 ul of Purdy 10% Maple tree | Maybe sap appears to decrease | Processed at room temperature, placed between 43 F. gel packs, and then flash frozen. Feb. 24, 2016 Pink straw |

TABLE 1-continued

| | | | | |
|---|---|---|---|---|
| | Holder #4 Pink soda straw, Feb. 24, 2016 Holder #4 Pink soda straw. | | sap. | Holder #5 Thawed in an ice water bath at 41 F. No movement, no pH done, Cells very distorted. Had a Live27/73 Dead stain. Feb. 24, 2016 Pink soda straw Holder #4 Thawed in an ice water bath at 41 F. Almost no movement and cells very distorted. Had a Live 29/71 Dead stain. Feb. 24, 2016 Pink soda straw Holder #4 Thawed in ice water bath at 41 F. Less than 1% moving forward and cells were distorted. Live 36/64 Dead. |
| | | | movement = quiescence. Maybe = Same, Maybe = Same. | |
| 100 | May 16, 2015, Mar. 6, 2016, Mar. 7, 2016 Green straw from Holder #6, Mar. 13, 2016 Green straw from Holder #6. | Apr. 28, 2015 Odin | None | 70 ul of Semen plus 210 ul of Purdy BTE + 20% Maple tree sap 308 mOsm. | Maybe Quiescent, Maybe Quiescent, No, No | Processed at room temperature, placed between 43 F. gel packs, and then flash frozen. May 16, 2015 Thawed in ice water, 1-5% moving well but motility slows quickly. Live dead stain shows 39 live/61 dead, 30 live/70 dead. Hot plate on microscope appears to speed loss of motility. Mar. 6, 2016 Thawed in an ice water bath at 41 F. 10-15% motility swimming forward. Many of the cells are distorted due to the low osmolality. There is a Live 17/83 Dead stain. Mar. 7, 2016 Green straw. Thawed in an ice water bath. Had 1-2% moving. The cells are very distorted and it had a Live 20/80 Dead stain. Mar. 13, 2016 Thawed in an ice water bath and the cells are very distorted. Less than 1% motility and a Live 9/91 Dead stain. |
| 101 | May 3, 2015, Mar. 2, 2016 Yellow straw, Holder #6 | Apr. 29, 2015 Odin | None | 20 ul of Semen plus 60 ul Purdy 10%, Maple sap | Unknown as sample from holder #5 was lost | Mar. 2, 2016 Thawed in an ice water bath at 41 F. Yellow straw. Cells very deformed. Live 3/97 Dead stain. |

TABLE 1-continued

| | | | | | |
|---|---|---|---|---|---|
| 102 | May 10, 2015, Mar. 2, 2016 Orange straw from Holder #6, Mar. 6, 2016 Orange straw from Holder #6. | Odin | Apr. 30, 2015 | None | 52 ul of Semen plus 104 ul of Purdy 5% Maple Sap | from straw., Maybe Maybe, Maybe-Many swollen and distorted cells. | Processed at room temperature, placed between 43 F. gel packs, for 2 minutes and then flash frozen. May 10, 2015 Thawed in 70 F. water bath, Live dead stain; 28 live/72 dead, Mar. 2, 2016 Orange soda straw. Thawed in an ice water bath at 41 F. Had 10% forward motility with many deformed cells. The speed of motility increased with warming. It had a Live 33/67 Dead stain. Mar. 6, 2016 Thawed in an ice water bath at 41 F. It had 10-15% forward motility and many distorted and swollen cells. Live 21/79 Dead. Motility speed increased with warming. |
| 103 | May 3, 2015, May 10, 2016, Mar. 21, 2016 Green straw Holder #6, Mar. 13, 2016 Green straw Holder #6 | Odin | Apr. 30, 2015 | None | 65 ul of Semen, plus Purdy 10% Maple Sap, plus 5% (13 ul) of DMA, No acclimation | NO, maybe, Yes = Quiescent, Yes = Quiescent | No acclimation in the fridge. Flash frozen. Thawed May 3, 2015 in Ice water, pH 7.5, 0% motility, no live dead stain done, Sample thawed May 10, 2015 Ice water bath, pH 7, 2-3% motility, Live Dead Stain Live 23/Dead 77. Mar. 2, 2016 Thawed in an ice water bath at 41 F. Saw 2% motile Almost no gross cell deformity with a Live 52/48 Dead stain. The longer it warmed on the plate the higher the motility up to 4%. Mar. 13, 2016 Thawed in an ice water bath at 41 F. Less than 1% motility. Little cell distortion and a Live 20/80 Dead stain. |
| 104 | May 3, 2015 | Odin | May 1, 2015 | None | 8 ul of Semen plus 8 ul Purdy 10% | No | May 3, 2015 Cells do not do well with this at room temperature. Thawed in ice water, less than 2% |

| | | | | | |
|---|---|---|---|---|---|
| 105 | Apr. 4, 2016, Apr. 8, 2016, Apr. 10, 2016 | Odin | None | 55 ul of Semen; plus 55 ul of BTE with/out fructose plus ½% Sucrose; plus 55 ul of BTE w/o Fruc + 1st Run maple tree sap, Tree #3. 2015 | Maybe; Mistake made adjusting pH up in 2nd media used - using Bicarb changing the pH from 6.48 to 7.23. This appears to impair motility. (Bad). Used 30 drops of Bicarb from a low dose insulin syringe to a 10 cc tube. | Maple tree sap plus Arabogalactin, (No MA), Plus Purdy 10% Maple Sap plus Arabogalactin plus 12% MA | motile. No live/dead stain done. Apr. 4, 2016 Thawed in a ice water bath. No motility and has a Live 54/46 Dead stain. Apr. 8, 2016 Thawed in an ice water bath at 41 F. and then palmed to warm. No motility with a Live 4/96 Dead stain. Apr. 10, 2016 Thawed in an ice water bath at 41 F. No motility with a Live 12/88 Dead stain. |
| 106 | Apr. 3, 2016, Apr. 8, 2016, Apr. 10, 2016 | | None | 50 ul of Semen; 50 ul of BTE - Fruc + ½% Suc; Plus 100 ul of BTE - Fruc + 1st Run Maple tree sap. 2015 | Maybe; Mistake made adjusting pH up in 2nd media used - using Bicarb changing the pH from 6.48 to 7.23. | | Apr. 3, 2016 Acellular, pH of 8 on tape, No cells seen on L/D stain. Apr. 8, 2015 Ice water thaw and then palmed to warm. pH near 8 on tape. No cells seen, lysed. No L/D stain. Apr. 10, 2016 Ice water thaw, pH near 7.5 on tape. No motility seen. Live 21/79 Dead. |

TABLE 1-continued

| | | | | |
|---|---|---|---|---|
| 107 | Apr. 8, 2016, Apr. 4, 2016, Apr. 8, 2016 | Odin | None | 47 ul of Semen; Plus 23 ul of BTE - Fruc + ½% Suc; Plus 65 ul of BTE - Fruc + 1st run Maple Tree sap. 2015 | This appears to impair motility. (Bad). Used 30 drops of Bicarb from a low dose insulin syringe to a 10 cc tube. Maybe; Mistake made adjusting pH up in 2nd media used - using Bicarb changing the pH from 6.48 to 7.23. | Apr. 4, 2016 Ice water thaw, pH 7 on tape. Live 53/47 Dead stain. Apr. 8, 2016 Ice water thaw and then palmed to warm. pH on tape was 7.2. No motility. Live 15/85 Dead stain. Apr. 8, 2016 Ice water thaw and then palmed to warm. pH 7.5 on tape. Live 13/87 Dead. |
| 108 | Apr. 4, 2016, Apr. 10, 2016, Apr. 10, 2016 | Odin | None | 40 ul Semen; Plus 20 ul of BTE - Fruc + ½% Suc; Plus 40 ul of BTE - Fruc + 1st Run Maple Tree #3. | This appears to impair motility. (Bad). Used 30 drops of Bicarb from a low dose insulin syringe to a 10 cc tube. Maybe; Mistake made adjusting pH up in 2nd media used - using Bicarb changing | Apr. 4, 2016 Capillary tube lost from straw in the tank. Apr. 10, 2016 Ice water thaw. No motility. pH of 7.2. No L/D stain. Apr. 10, 2016 Ice water thaw. pH 7.2 on tape. Less than 1% motile. Live 24/76 Dead. |

| | | | | |
|---|---|---|---|---|
| | | | TABLE 1-continued | |
| | | | | 2015 | the pH from 6.48 to 7.23. This appears to impair motility. (Bad). Used 30 drops of Bicarb from a low dose insulin syringe to a 10 cc tube. | |
| 109 | Apr. 4, 2016, Apr. 4, 2016, Apr. 10, 2016, Apr. 10, 2016 | Mar. 27, 2016 | Odin | None | 40 ul of Semen; Plus 40 ul of BTE - Fruc + ½% Suc; Plus 80 ul of BTE - Fruc + 1st Run Maple Tree #3. 2015 | Maybe; Mistake made adjusting pH up in 2nd media used - using Bicarb changing the pH from 6.48 to 7.23. This appears to impair motility, (Bad). Used 30 drops of Bicarb from a low dose insulin syringe to a 10 cc tube. | Apr. 4, 2016 Ice water thaw, pH 8 on tape. No motility and a Live 30/70 Dead stain. Apr. 4, 2016 Ice water thaw. pH on tape of 7.2. No motility. Live 30/70 Dead stain. Apr. 10, 2016 Ice water thaw with pH of 7.5 on tape. No motility and a Live 19/81 Dead stain. Apr. 10, 2016 Ice water thaw pH of 7.5. |
| 110 | Apr. 3, 2016, Apr. 5, 2016, Apr. 10, 2010 | Mar. 28, 2016 | Odin | None | 30 ul of Semen; Plus 30 ul of BTE - Fruc + ½ % Suc; Plus BTE - Fruc + 1st | Maybe; Mistake made adjusting pH up in 2nd media used - | Apr. 3, 2016 Ice water thaw, pH on tape 7.2. No motility. Live 51/49 Dead stain. Apr. 5, 2016 Ice water thaw, pH of 7 on tape. No motility. Live 5/95 dead stain. |

TABLE 1-continued

| | | | | |
|---|---|---|---|---|
| | | | Run Maple Tree sap 2015 | using Bicarb changing the pH from 6.48 to 7.23. This appears to impair motility. (Bad). Used 30 drops of Bicarb from a low dose insulin syringe to a 10 cc tube. | Apr. 10, 2016 Ice water thaw. pH of 7.2 on tape. No motility. Live 16/84 Dead stain. |
| 111 | Apr. 4, 2016, Apr. 8, 2016, Apr. 8, 2016 | Mar. 28, 2016 | Odin | None | 40 ul of Semen; Plus 40 ul of BTE - Fruc + ½% Suc; Plus 60 ul of BTE - Fruc + 1st Run Maple Tree #3. 2015 | Maybe; Mistake made adjusting pH up in 2nd media used - using Bicarb changing the pH from 6.48 to 7.23. This appears to impair motility. (Bad). Used 30 drops of Bicarb from a low dose insulin syringe to a 10 cc tube. | Apr. 4, 2016 Ice water thaw, pH of 7.2 on tape. No motility and a Live 35/65 Dead stain. Apr. 8, 2016 Ice water thaw and then palmed to warm. pH of 7.2 on tape. Live 5/95 Dead, Apr. 8, 2016 Less than 1% motility on ice water thaw. pH 7.2 on tape. Live 7/93 Dead. |
| 112 | Apr. 4, 2016, Apr. 5, 2016, Apr. 5, 2016 | Mar. 30, 2016 | Odin | None | 42 ul of Semen; Plus 42 ul of BTE, no fructose + | Yes, one sample did very well and I wonder if | Apr. 4, 2016 Ice water thaw. pH of 7.5 on tape. Live 25/75 Dead stain. Apr. 5, 2015 Ice water thaw and then palmed, 50% |

TABLE 1-continued

| | | | | | |
|---|---|---|---|---|---|
| | | | | ½% Suc (pH 7.4); Plus 65 ul of BTE - Fruc + plus 1st Run Maple Tree Sap from Tree #3 (2015), (pH 7.23) | it froze more slowly. | motile, pH 7.5 on pH tape, Live 53/47 Dead stain. Apr. 5, 2016 Ice water thaw and then palmed to warm. No motility. Live 8/92 Dead. Need slow freeze and at least 30% sap for the cells to survive. pH adjustments bad on these samples. |
| 113 | Apr. 4, 2016, Apr. 5, 2016, Apr. 8, 2016 | Odin | None | 35 ul of Semen; Plus 35 ul of BTE - Fruc + ½% Suc (pH 7.4); Plus 35 ul of BTE - Fruc + 1st Run Maple Tree sap tree #3, 2015, (pH 7.23) | Maybe; pH adjustment in both diluents is stressing the cells too much and stops motility. | Apr. 4, 2016 Ice water thaw, no cells seen. No pH done. No L/D stain. Apr. 5, 2016 Ice water thaw. No motility. No pH done. Live 19/81 Dead stain. Apr. 8, 2016 Ice water thaw. pH 7.3. No motility. Live 12/88 Dead stain. |
| 114 | Apr. 4, 2016, Apr. 5, 2016, | Odin | None | 25 ul of Semen; Plus 25 ul BTE - Fruc + ½% Suc (pH 7.4); Plus 35 ul of BTE - Fruc + 1st Run Maple tree sap (pH 7.23). No other cryoprotectant. | Maybe; the pH and speed of freezing need to be changed. Slow the freeze down and lower the pH to decrease cell metabolism. | Apr. 4, 2016 Ice water thaw with no motility. pH 8 on tape. Live 26/73 Dead stain. Apr. 5, 2016 Ice water thaw and no motility. pH of 7.4 on tape. Live 10/90 Dead stain. Too little sap was used and the freezing needs to be slow. pH needs to be lower in starting extenders. |
| 115 | Apr. 3, 2016, Apr. 5, 2016, Apr. 5, 2016, Apr. 5, 2016 | Odin | None | 65 ul Semen; Plus 65 ul of BTE - Fruc = ½% Suc (pH 7.4); Plus 65 ul BTE - Fruc + 1st Run Maple Tree sap. | Maybe; the pH and speed of freezing need to be changed. Slow the freeze down and | Apr. 3, 2016 Ice water thaw, pH on tape 7.4. No motility and a Live 17/84 Dead stain. Percentage of sap needs to increase from 33%. Apr. 5, 2016 lost sample as the caulk came out on thawing. Apr. 5, 2016 Ice water thaw and then palmed to warm |

TABLE 1-continued

| | | | | | |
|---|---|---|---|---|---|
| 116 | Apr. 4, 2016, Apr. 4, 2016, Apr. 4, 2016 | Odin | None | 40 ul of Semen; Plus 40 ul of Goshawk Semen Extender = BTE − Fruc + ½% Suc w/pH of 6.27.: Plus 80 ul BTE − Fruc + Amur Maple + Glutathione + NN- Bis . . . Sulfonic Acid | 2015 (pH 7.23) lower the pH to decrease cell metabolism. NO, NO, NO, Formula error stopping motility in samples. The addition of glutathione and NN- Bis . . . sulfonic acid should not have been done. | because caulk came out. pH 7.5 on tape. No motility. Live 8/92 Dead stain. Apr. 5, 2016 Ice water thaw and then palmed to warm. pH 7.2. No motility. Live 6/94 Dead, Apr. 4, 2016 Ice water thaw. pH of 7. Live 0/100 Dead stain. No motility. Apr. 4, 2016 Ice water thaw. pH of 7. Live 25/75 Dead stain. No motility. Apr. 4, 2016 Ice water thaw. pH of 7. Live 9/91 Dead stain. No motility. |
| 117 | Apr. 4, 2016, Apr. 4, 2016, Apr. 4, 2016 | Odin | None | 40 ul Semen; Plus 40 ul Goshawks Extender (pH 6.27); Plus 80 ul of BTE − Fruc + Amur Maple 1st run. + Glutathione + NN Bis . . . sulfonic acid. | NO, NO, NO, Formula error stopping motility in samples. The addition of glutathione and NN- Bis . . . sulfonic acid should not have been done. | Apr. 4, 2016, Ice water thaw, pH 7, No motility. Live 28/72 Dead. Apr. 4, 2016 Ice water thaw. pH 7. No motility. Live 0/100 Dead stain. Apr. 4, 2016 Ice water thaw. pH 7, No motility. Sample too small for a Live/Dead stain. 1 straw missing. |
| 118 | Apr. 5, 2016, ( ) | Odin | None | 33 ul Semen; Plus 66 ul BTE − Fructose + Maple tree sap tree #3 | Yes, simple addition of sap allowed the cells to | Brix value 2.5 Apr. 5, 2016 Ice water thaw, pH on tape was 7, 15-20% moving initially. Live 47/Dead 53. Longer acclimation may have increased survival. But longer acclimation |

TABLE 1-continued

| | | | | | |
|---|---|---|---|---|---|
| | | | | survive. | decreases survival in the hen's seminal tubules when it does not have an extender added. |
| 119 | Apr. 10, 2016, Apr. 11, 2016, ( ). | Apr. 5, 2016 | Odin | 2015. Did not acclimate with an extender. Only acclimated semen in its own tube and then added the sap. Back to the 2015 Formulas. The modification that I made to the pH was stopping motility in the cells so I started back at baseline extenders. 45 ul Semen; Plus 45 ul of BTE - Fructose + ½% Sucrose (pH 7.51); Plus 90 ul of BTE - Fructose + Maple Tree #3 2015 (pH 6.48) | Yes, Yes | Brix value 2.5 | Apr. 10, 2016, Ice water thaw, pH 7 on test tape, About 5% vibrating in place, Live 30/Dead 70. Would likely have done better if left above the vapors longer. Apr. 11, 2016 Ice water thaw, pH 7 on tape, Some vibrating in place but not moving forward, Live 31/Dead 69. It takes 90 seconds to process 1 sample into 4 tubes. |
| 120 | Apr. 10, 2016 | Apr. 8, 2016 | Odin | Back to the 2015 Formulas. The modification that I made to the pH was stopping motility in the cells so I started | Yes, the original 2015 sap formulas support the cells well. | | Apr. 10, 2016 Ice water thaw, pH 7, 50% initially motile to about 5% motile over about 10 minutes. Live 62/Dead 38. It took 90 seconds to package the 4 straws and this delay in getting it into the LN2 likely allowed the osmotic gradient across the cells to fade, allowing the cell to rehydrate prior to the |

TABLE 1-continued

| | | | | |
|---|---|---|---|---|
| | | | | back at baseline extenders. 45 ul Semen, then 45 ul of BTE - Fructose + ½% Sucrose (pH 7.51), then added 90 ul of BTE - Fructose + Maple Tree #3 2015 | freeze. This is conjecture, but noted as a problem in references. Need a processing time less than this. I stored a small sample of this tube in the fridge from 7:30 AM to 1:30 AM and more than 75% were moving forward and straight. (not frozen). |
| 121 | Apr. 6, 2016 | Odin | Back to the 2015 Formulas. The modification that I made to the pH was stopping motility in the cells so I started back at baseline extenders. 55 ul Semen; Plus 55 ul of BTE - Fructose + ½% Sucrose (pH 7.51); Plus 100 ul of BTE - Fructose + Maple Tree #3 2015 (pH 6.48) | Brix value 2.5 |
| 122 | Apr. 7, 2016 | Odin | Back to the 2015 Formulas. The modification that I made to | Brix value 2.5 |

TABLE 1-continued

| | | | | |
|---|---|---|---|---|
| | | | the pH was stopping motility in the cells so I started back at baseline extenders. | |
| 123 | Apr. 8, 2016 | Odin | Back to the 2015 Formulas. The modification that I made to the pH was stopping motility in the cells so I started back at baseline extenders. | Brix value 2.5 |
| 124 | Apr. 7, 2015 | Odin | Back to the 2015 Formulas. The modification that I made to the pH was stopping motility in the cells so I started back at baseline extenders. | Brix value 2.5 |
| 125 | Apr. 8, 2016 | Odin | Back to the 2015 Formulas. The modification that I made to the pH was stopping motility in the cells so I started back at baseline extenders. | Brix value 2.5 |

TABLE 1-continued

| | | | | | |
|---|---|---|---|---|---|
| 126 | Apr. 10, 2016, Apr. 11, 2016 | Odin | Back to the 2015 Formulas. The modification that I made to the pH was stopping motility in the cells so I started back at baseline extenders. 40 ul Semen; Plus 40 ul of BTE - Fructose + ½% Sucrose 2015 (pH 7.51); Plus 80 ul BTE - Fructose + Maple Tree sap #3 2015 (pH 6.48). | Maybe, YES | Brix value 2.5 | Holder #4 trace sample because caulk came out of capillary tube, Thawed in Ice Water, No pH, No L/D stain. 10% moving forward with good motility.; Apr. 11, 2016 Ice water thaw, pH 7, 30% motile on visual inspection, Live 50/Dead 50. |
| 127 | Apr. 10, 2016 | Odin | Back to the 2015 Formulas. The modifications that I made to the pH was stopping motility in the cells so I started back at the baseline extenders. BIRCH sap STARTS HERE. 40 ul Semen, plus 40 ul of BTE - Fructose + | | | |

TABLE 1-continued

| | | | | | pH of Diluent | Diluent Type | | | | |
|---|---|---|---|---|---|---|---|---|---|---|
| 128 | Apr. 10, 2016 | Apr. 10, 2016 | Odin | 1st Run Alaska Birch (pH. 7.56), then added 40 ul BTE - Fructose + Maple Tree #3 2015 (pH. 6.48). 40 ul Semen; Plus 40 ul BTE - Fructose + 1st run Alaska Birch (pH. 7.56); Plus 40 ul BTE - Fructose + Maple Tree sap tree #3 2015 (pH. 6.48). | | Yes | | | | Apr. 10, 2016 Ice water thaw, pH 7 on tape, 25% moving straight forward, Live 57/43 Dead stain. |

| Number | How sample was frozen. | pH of Diluent | Diluent Type | Holder in tank it is located in | Straw Type. | How storage straw performed. |
|---|---|---|---|---|---|---|
| 4 | Either flash frozen or suspended above the liquid nitrogen for 30 seconds prior to immersion. | 9.1 | Diluent #1 | Unknown. | Unknown | |
| 5 | Flash frozen. | 9.1 | Diluent #1 | 2 Unknown. | Unknown Natellson Capillary tube with 2 caps. | This straw for storage stored well and did not explode. |
| 6 | Either flash frozen or suspended above the liquid nitrogen for 30 seconds prior to immersion. | 9.1 | Diluent #1 | | | |
| 7 | Either flash frozen or suspended above the liquid nitrogen for 30 seconds prior to immersion. | 9.1 | Diluent #1 | Unknown. | Unknown | |
| 8 | Flash frozen. | 8.86 | Diluent #2 | 2 Unknown. | Unknown Unknown | |
| 9 | Either flash frozen or suspended above the liquid nitrogen for 30 seconds prior to immersion. | 8.86 | Diluent #2 | | | |
| 10 | Flash frozen. | 8.86 | Diluent #2 | 2 | | |

TABLE 1-continued

| | | | | | | |
|---|---|---|---|---|---|---|
| 11 | Either flash frozen or suspended above the liquid nitrogen for 30 seconds prior to immersion. | 8.86 | Diluent #2 | Unknown | Unknown | |
| 12 | Flash frozen. | 8.86 | Diluent #2 | 2 | Unknown | |
| 13 | Either flash frozen or suspended above the liquid nitrogen for 30 seconds prior to immersion. | 8.86 | Diluent #2 | Unknown | Unknown | |
| 14 | Either flash frozen or suspended above the liquid nitrogen for 30 seconds prior to immersion. | 9.08 | Diluent #3 | Unknown | Unknown | |
| 15 | Either flash frozen or suspended above the liquid nitrogen for 30 seconds prior to immersion. | Unknown | None | Unknown | Unknown | |
| 16 | Either flash frozen or suspended above the liquid nitrogen for 30 seconds prior to immersion. | 9.08 | Diluent #3 | Unknown | Unknown | |
| 17 | Flash frozen. | 9.08 | Diluent #3 | 3 | Natelsson Capillary tube with 2 caps. | This straw for storage stored well and did not explode. |
| 18 | Flash frozen. | 9.18 | Diluent #4 | 2 | Natelsson Capillary tube with 2 caps. | |
| 19 | Either flash frozen or suspended above the liquid nitrogen for 30 seconds prior to immersion. | 7.06 | Trout | Unknown | Natelsson Capillary tube with 2 caps. | |
| 20 | Either flash frozen or suspended above the liquid nitrogen for 30 seconds prior to immersion. | 7.06 | Trout | Unknown | Natelsson Capillary tube with 2 caps. | Exploded and lost. |
| 21 | Flash frozen. | 7.06 | Trout | 2 | Natelsson Capillary tube with 2 caps. | |
| 22 | Flash frozen. | 7.06 | Trout | 5 | Unknown | |
| 23 | Suspended over liquid nitrogen for 30 seconds to exposed to liquid | 7.16 | Trout #2 | Unknown | Natelsson Capillary tube with 2 | This straw for storage stored well |

TABLE 1-continued

| | | | | | |
|---|---|---|---|---|---|
| | | | | caps. | and did not explode. |
| 24 | Suspended over liquid nitrogen for 30 seconds to exposed to liquid nitrogen vapors and then flash frozen. | 7.16 | Trout #2 | Floating on liquid nitrogen and lost out of holder. | Natelson Capillary tube with 2 caps. Exploded on thaw but did not lose the sample. |
| 25 | Flash frozen. | 7.16 | Trout #2 | 5 | Unknown |
| 26 | Flash frozen. | 7.16 | Trout #2 | 5 | Unknown |
| 27 | Flash frozen. | 7.16 | None | 5 | Unknown |
| 28 | Flash frozen. | 7.16 | Trout #2 | 5 | Unknown |
| 29 | Suspended over liquid nitrogen for 30 seconds to exposed to liquid nitrogen vapors and then flash frozen. | 7.14 | Milk #1 | Unknown. | Natelson Capillary tube with 2 caps. This straw for storage stored well and did not explode. |
| 30 | Flash frozen. | 7.42 | Trout #2 plus Sorbitol and Arabogalactin. | 5 | Unknown |
| 31 | 10 mm of semen to 45 mm of Turkey Extender, Acclimated in the fridge for 30 minutes. Added 3 ul (units) of DMA. Hung in vapors for 10 minutes the placed in liquid nitrogen. | | Turkey Extender plus DMA | 6 | Commercial semen straw with button caps. Exploded and lost. |
| 32 | Semen acclimated in fridge for 30 minutes, then DMA added, then hung over vapors for 10 minutes, then immersed in liquid nitrogen. | | Turkey Extender plus (6%) DMA | 6 | Commercial semen straw with button caps. GREEN ON TOP OF ALUMINUM HOLDER. FOUND FLOATING IN TANK MINUS LABEL |
| 33 | Semen acclimated in fridge for 30 minutes, then DMA added, then hung over vapors for 10 minutes, then immersed in liquid nitrogen. | | Turkey Extender plus DMA | 6 | Commercial semen straw with button caps. GREEN ON TOP OF ALUMINUM HOLDER. FOUND FLOATING IN TANK MINUS LABEL |

TABLE 1-continued

| | | | | |
|---|---|---|---|---|
| 34 | Semen acclimated in fridge for 30 minutes, then DMA added, then hung over vapors for 10 minutes, then immersed in liquid nitrogen. | Turkey Extender plus DMA | 6 | Commercial semen straw with button caps. GREEN ON TOP OF ALUMINUM HOLDER. | FOUND FLOATING IN TANK MINUS LABEL |
| 35 | Semen acclimated in fridge for 30 minutes, then DMA added, then hung over vapors for 10 minutes, then immersed in liquid nitrogen. | Turkey Extender plus DMA | 6 | Commercial semen straw with button caps. GREEN ON TOP OF ALUMINUM HOLDER. | Exploded and not lost. But explosion was loud and semen cells likely damaged due to trauma. I am guessing that this sample went to Juniper because 4 were found floating free on top of the liquid nitrogen and not labeled. |
| 36 | See prior note | Turkey Extender plus DMA | 6 | Unknown | |
| 37 | Flash frozen. | Turkey Extender plus DMA | 5 | Commercial semen straw with button caps. RED ON TOP OF ALUMINUM HOLDER | Exploded and lost. |
| 38 | Flash frozen. | Turkey Extender plus (10%) DMA | 5 | Commercial semen straw with button caps. RED ON TOP OF | Exploded and lost. |

TABLE 1-continued

| | | | | | |
|---|---|---|---|---|---|
| 39 | Flash frozen. | | Turkey Extender plus (10%) DMA | 5 | ALUMINUM HOLDER Commercial semen straw with button caps. RED ON TOP OF ALUMINUM HOLDER | Exploded and lost. |
| 40 | Flash frozen. | | Turkey Extender plus (18%) DMA | 5 | ALUMINUM HOLDER Commercial semen straw with button caps. RED ON TOP OF ALUMINUM HOLDER | Exploded and lost. The reinforced plastic coated glass capillary tubes withstand explosions. |
| 41 | SEE NOTES ON 2013 SAMPLES. | | Turkey Extender plus DMA | | | |
| 42 | In fridge 10 minutes to acclimate, plus 1.5 units DMA, above vapors for 10 minutes, immersed suddenly into LN2 | 6.74 | Turkey Extender plus DMA, 5% DMA | #2 | #42, white straw, Natellson tube, capped on 1 end firmly and outside end not capped. | |
| 43 | Acclimated in fridge 10 minutes, plus 1.5 units DMA (5%), hung over vapors for 10 minutes within 1 minute of adding DMA, dunked into LN2. | 6.74 | Turkey Extender plus DMA, 5% DMA | #2 | #43 White straw, standard capillary tube, plus two crito caps and 1 Natellson cap. | |
| 44 | Acclimated in fridge 10 minutes, plus 3 ul of DMA (6%). Acclimated in fridge for 10 minutes, suspended above the vapors 10 minutes, then dunked in LN2. | 6.74 | Turkey Extender plus 6% DMA | #2 | #44 White straw, standard capillary tube plus 2 critocaps and 1 Natellson cap. | Straw exploded on thaw, but one end stayed closed. |

TABLE 1-continued

| | | | | |
|---|---|---|---|---|
| 45 | Acclimated in fridge 10 minutes, plus 2 ul of DMA (10%), hung over vapors for 10 minutes, plunged into LN2 | 6.74 | Turkey extender plus 10% DMA | #2 | #45 White straw, Standard capillary tube, plus 2 caps on one end and clay on the far end. |
| 46 | Acclimated in fridge (35 F.). Plus 2 ul of DMA, hung over vapors for 10 minutes, plunged into LN2. | 6.74 | Turkey extender plus 10% DMA | #2 | #46 White straw, tube type not recorded. |
| 47 | Acclimated in fridge at 35 F. for 10 minutes, one sample hung over vapors for 7 minutes and the other 10 minutes, and then dunked into LN2. | 6.74 | Turkey Extender plus 6% DMA | #2 | #47, two tubes, White straw, Natellson tube, plus clay and Natellson cap on pointed end, and Natellson cap on top end. |
| 48 | Acclimated in the fridge at 35 F., 1.5 ul of DMA added, over vapors 10 minutes, dunked into LN2. | 6.74 | Turkey extender plus 7% DMA. | #2 | White straw, Natellson capillary tube plus clay in both ends and Natellson cap on pointed end. |
| 49 | Acclimated in fridge at 35 F. for 10 minutes, plus 3 ul of DMA, hung over vapors 10 minutes, plunged into LN2. | 6.74 | Turkey Extender plus 6% DMA | #2 | White straw, Natellson tube plus clay on both ends and rubber cap on pointed end. |
| 50 | Acclimated in fridge at 35 F. for 10 minutes, plus 2 ul of DMA (7%), over | 6.74 | Turkey extender plus 7% | #2 | White straw, 75 ul standard |

TABLE 1-continued

| | | | | |
|---|---|---|---|---|
| | vapors for 10 minutes, then plunges into LN2. | | DMA. | capillary tube plus 1 critocap and Natellson Cap on one end and Clay on the other end. |
| 51 | Acclimated in the fridge at 35 F., 1.25 (5%) DMA added, hung over vapors for 10 minutes, plunged into LN2. | 6.74 | Turkey extender with 5% DMA. | #2 White straw, 75 ul standard capillary tube plus one end a critocap and one end a Natellson cap. |
| 52 | Acclimated in the fridge at 35 F., 2.7 ul of DMA added, Hung over vapors 10 minutes, plunged into LN2. | 6.74 | Turkey extender with 6% DMA. | #2 White straw, Natellson Capillary tube, plus clay on both ends, and Natellson cap on pointed end. |
| 53 | Acclimated in the fridge at 35 F. for 15 minutes, 2.23 ul of DMA added, hung over vapors 10 minutes, plunged into LN2. | 6.74 | Turkey extender with 6% DMA. | #2 White straw, Natellson Capillary tube, plus clay on both ends, and Natellson cap on pointed end. |
| 54 | Acclimated in the fridge at 35 F. for 15 minutes, plus 1 ul of DMA (5%), hung over vapors 10 minutes, plunged into LN2. | 6.74 | Turkey extender with 6% DMA. | #2 White straw, Standard 75 ul capillary tube, clay on one end and Natellson |

TABLE 1-continued

| | | | | |
|---|---|---|---|---|
| 55 | Acclimated in the fridge at 35 F. for 15 minutes, added 2.5 ul DMA, hung over vapors 10 minutes, plunged into LN2. | 6.74 | Turkey extender with 5% DMA. | #2 | cap and critocap on other end. White straw, Natellson tube plus clay on pointed end and Natellson caps on both ends. |
| 56 | Acclimated in the fridge for 15 minutes, plus 1 ul of DMA (5%), hung over vapors for 10 minutes, plunged into LN2. | 6.74 | Turkey extender, with Maple Syrup, with 5% DMA. | #2 | Red Straw, Natellson tube, with clay and Natellson cap on pointed end and just clay on large end. |
| 57 | Acclimated in the fridge for 10 minutes, plus 1 ul of DMA (5%), dropped into the LN2. | | Turkey Extender by itself | #4 holder in Tank 2 | Red straw. This was a 75 ul mylar coated capillary tube, caulked on both ends, plus 2 critocaps, plus a teal cap on the semen end. The caps exploded off of the ends and most of the sample was lost. |
| 58 | Acclimated in the fridge for 15 minutes, plus 3 ul of DMA | | Beltsville Turkey Extender plus .2 mg Inositol to 10 ml of Extender. | #4 Holder in Second tank. | Red soda straw, with a 75 ul Mylar coated capillary tube, caulked on both ends, with two critocaps, and one teal cap. Plus aluminum holder. Sample explodes across the garage. |

TABLE 1-continued

| | | | | |
|---|---|---|---|---|
| 59 | Acclimated in the fridge for 15 minutes, Plus 2.6 ul of DMA and then flash frozen. | Beltsville Turkey Extender plus .2 mg Inositol to 10 ml of Extender. | #4 Holder in the Second tank | Red soda straw, with a 75 ul Mylar coated capillary tube, caulked on both ends, with two critocaps, and one teal cap. With Aluminum holder. | Tube performed well. |
| 60 | Acclimated in the fridge for 15 minutes and then flash frozen | Beltsville Turkey Extender plus .2 mg Inositol to 10 ml of Extender. | #4 Holder in the Second tank | Red soda straw, with a 75 ul Mylar coated capillary tube, caulked on both ends, with two critocaps, and one teal cap. With Aluminum holder. | Exploded but kept sample. |
| 61 | Acclimated in the fridge for 15 minutes and then flash frozen | Beltsville Turkey Extender plus .2 mg Inositol to 10 ml of Extender. | #3 Holder, Tank 2 | Red soda straw, with a 75 ul Mylar coated capillary tube, caulked on both ends, with two critocaps, and one teal cap. | Straw performed well. |
| 62 | Acclimated in the fridge for 15 minutes and then flash frozen | Beltsville Turkey Extender plus .2 mg Inositol to 10 ml of Extender. | #3 Holder, Tank 2 | Red soda straw, with a 75 ul Mylar coated capillary tube, caulked on | Straw exploded on thaw, but sample was preserved. |

TABLE 1-continued

| | | | | |
|---|---|---|---|---|
| 63 | Acclimated in the fridge for 15 minutes and then flash frozen | Beltsville Turkey Extender plus .2 mg Inositol to 10 ml of Extender. | #3 Holder, Tank 2 | White soda straw, with a Mylar coated capillary tube, caulked on both ends, with two critocaps, and one teal cap. | Tube performed well. |
| 64 | Acclimated in the fridge for 15 minutes and then flash frozen | Beltsville Turkey Extender plus .2 mg Inositol to 10 ml of Extender. | #3 Holder, Tank 2 | Red soda straw, with a 75 ul Mylar coated capillary tube, caulked on both ends, with two critocaps, and one teal cap. | Tube exploded, Lost most of the sample. |
| 65 | Acclimated in the fridge for 15 minutes and then flash frozen | Beltsville Turkey Extender plus .2 mg Inositol to 10 ml of Extender. | #3 Holder, Tank 2 | Red soda straw, with a 75 ul Mylar coated capillary tube, caulked on both ends, with two critocaps, and one teal cap. | Tube performed well. |
| 66 | Acclimated in the fridge for 15 minutes and then flash frozen | Beltsville Turkey Extender plus .2 mg Inositol to 10 ml of Extender. | #3 Holder, Tank 2 | White soda straw, with a Mylar coated capillary tube, caulked on both ends, with two critocaps, | Straw empty on thaw. |

TABLE 1-continued

| | | | | |
|---|---|---|---|---|
| 67 | No acclimation. Flash Frozen. | SAP Beltsville Turkey Extender minus the fructose, plus Maple Tree sap, first run, Tree number 3. | #2 Holder Tank 2 | Orange soda straw, with 75 ul capillary tube, plus clay both ends, plus critocaps. and one teal cap, No sample in tube on thaw. | Trace sample left on thaw due to exploding. |
| 68 | No acclimation, flash frozen. | Likely same as samples above and below this line. | #3 Holder, Tank 2 | Red soda straw, in Aluminum sleeve, with 75 ul mylar capillary tube, w/ clay and critocap with teal cap 1 end, and clay and crito cap other end. | Straw performed well. Did not explode. |
| 69 | No acclimation was done and it was flash frozen. It was carried to the garage on cold gel packs. | SAP, BTE, no fructose, plus Maple Tree sap, first run, Tree number 3. | #2 holder, Tank 2. | Aluminum sleeve with a White soda straw, with 75 ul capillary tube, 1 end left open, other end capped with clay, 1 critocap, 1 teal cap. | This straw did well and did not explode, but the large teal caps on the end is slow to thaw. The open end is key to this success. |
| 70 | No acclimation was done and it was flash frozen. It was carried to the garage on cold gel packs. | SAP, BTE, no fructose, plus Maple Tree sap, first run, | #2 holder, Tank 2. | Red soda straw with holes, plus plastic poultry straw, with a 75 ul | Straw performed well, did not explode. |

TABLE 1-continued

| | | | | |
|---|---|---|---|---|
| 71 | No acclimation was done and it was flash frozen. It was carried to the garage on cold gel packs. | SAP, BTE, no fructose, plus Maple Tree sap, first run, Tree number 3. | #2 holder, Tank 2. | capillary tube, 1 end left open, the other end is clayed, slid into poultry straw with cotton facing down. Straw is ventilated. Red soda straw with holes, plus plastic poultry straw, with a 75 ul capillary tube, 1 end left open, the other end is clayed, slid into poultry straw with cotton facing down. | |
| 72 | No acclimation was done and it was flash frozen. It was carried to the garage on cold gel packs. | SAP, BTE, no fructose, plus Maple Tree sap, first run, Tree number 3. | #2 holder, Tank 2. | Red soda straw with holes, plus plastic poultry straw, with a 75 ul capillary tube, 1 end left open, the other end is clayed, slid into poultry straw with cotton facing down. | Straw performed well. |
| 73 | No acclimation was done and it was flash frozen. | SAP, BTE, no fructose, plus | #1 holder, Tank #2 | Pink soda straw, plus a plastic poultry | Straw performed well. It did not |

TABLE 1-continued

| # | Notes | Sample | Holder | Container |
|---|---|---|---|---|
|  |  | BIRCH tree sap. Sucrose is lower than Maple tree sap. |  | straw, plus a 75 ul capillary tube with 1 end sealed with clay, with cotton on poultry straw facing down. Number on straw reads 67. explode. |
| 74 | 2 samples were produced due to the volume of the sample. Both were flash frozen. No gel packs were used. | 16% MA used as half of the sample so the final concentration of the MA was 8%. | Holder #3 in Can #1. | Orange (#68 on straw) and Pink soda straws (# 68 on straw), with a plastic poultry straw inside, with a 75 ul mylar capillary tube clayed on one end, with cotton on poultry straw facing down. |
| 75 | Separated into 3 straws as it was so large. On gel packs less than 2 minutes and then flash frozen. | 16% MA used as half of the sample so the final concentration of the MA was 8%. | #3 Holder Tank #1. | 3 green soda straws, no holes cut in them. Plastic poultry straws with 75 ul mylar capillary tubes, 1 end has clay, the cotton on the poultry straw faces down. |

TABLE 1-continued

| | | | | | |
|---|---|---|---|---|---|
| 76 | Acclimated in the fridge for 10 minutes, DMA added, used bottom of fridge at 40 F. AND TURNED DOWN THE FRIDGE FOR THE FIRST TIME so it went up in temperature. THE TOP OF THE FRIDGE WAS AT 35 F. AND THE BOTTOM OF THE FRIDGE WAS AT 40 F. BEFORE I TURNED IT DOWN. It now sits at 42 at the bottom where I am now holding the samples so it is 9 degrees warmer for processing. The samples done from here out are done at a warmer temperature. | 7.5 on pH tape after thaw. | Beltsville Turkey Extender, no fructose, plus ½% sucrose. | #3 Holder Tank #1. | Soda straw plus plastic poultry straw, plus a 75 ul mylar capillary tube with clay on 1 end. With cotton on poultry straw facing down. Not ventilated. Blue in color. |
| 77 | Flash frozen after 10 minutes of acclimation at 41 F. | 7.5 pH on pH tape after thaw. | BTE, no fructose, plus ½% sucrose, and DMA | Holder #3 in Can #1. | 3 soda straws, light green, dark green, orange, with a poultry straw inside that and a 75 ul mylar tube inside of that. Green straw was not ventilated and the Orange straw was not ventilated. |
| 78 | Flash frozen after 10 minutes of acclimation at 41 F. | | BTE, no fructose, plus Birch Tree sap. | Holder #3 in Can #2. | 2 soda straws, both pink, both ventilated, with poultry straw and a 75 ul mylar capillary tube inside | Storage with a Ventilated soda straw, poultry straw inside that [Poultry straw crimped on |

TABLE 1-continued

| | | | | |
|---|---|---|---|---|
| 79 | Sample was not acclimated in the fridge. It was mixed, placed in tubes, and then put between gel packs from the fridge, carried out to the LN2 can, and flash frozen. | Birch tree sap in BTE, No fructose | Holder #3, Tank #2. | 2 Soda straws, one yellow and one green, both ventilated with holes; with a poultry straw, cotton facing down, crimped on top end; with 75 ul capillary tubes, clayed on one end. that. Clay on one end leaving it open on top. top end and cotton on the bottom end], with a 75 ul mylar coated capillary tube, clay on one end only with the other end left open to LN2; Performed the BEST Keep the material open so they do not explode. All samples stored this way from this point on. Well, no problems. |
| 80 | Acclimated in the fridge for 10 minutes in separate tubes, then combined and packaged, then flash frozen | Maple tree sap in BTE, no fructose. | Holder #3, Tank #2. | 2 soda straws, one orange and one pink, both Well, no problems. |

TABLE 1-continued

| # | Procedure | Sap/pH | Straws/Holder | Result |
|---|---|---|---|---|
| 81 | Acclimated for 10 minutes in the fridge at 41 F, and then flash frozen | | Maple tree sap in BTE, no fructose. | Holder #3, Tank #2. | ventilated, with poultry straw inside, with 75 ul mylar coated capillary tube inside. 2 Soda straws that were ventilated, with poultry straw inside, cotton end down; 75 ul mylar capillary tube, clay on one end | Well, no problems. |
| 82 | Semen and BTE – Fruc, + ½% sucrose acclimated in separate tube from Birch sap BTE, at 42 F. in fridge for 10 minutes, combined, then packaged in 4 tubes, 75 ul capillary tube, caulked one end; placed in poultry straw, cotton down; inside ventilated soda straw. 4 straws made. All green soda straws. | pH on pH tape after thaw was 7.0, 7.2, 7.0, 7.5. | Birch tree sap in BTE, No fructose | 2 straws in Holder #6 tank 1, and 2 straws in Holder #5 tank 1. | 4 green soda straws that were ventilated, 75 ul mylar capillary tube, inside poultry straw, inside ventilated soda straw. | Does not explode but thaws too slowly. |
| 83 | Semen and BTE – Fruc, + ½% sucrose acclimated in separate tube from Maple tree sap BTE, at 42 F. in fridge for 10 minutes, combined, then packaged in 4 tubes, 75 ul capillary tube, caulked one end; placed in poultry straw, cotton down; inside ventilated soda straw. 3 straws made. 3 Yellow straws. | pH on pH tape after thaw was 7.5-8, 7.0, 7.0 | Maple tree sap in BTE, no fructose. | 2 straws in Holder #6 tank 1, and 1 straws in Holder #5 tank 1. | 3 yellow soda straws that were ventilated, 75 ul mylar capillary tube, inside poultry straw, inside ventilated soda straw. | Good |
| 84 | Semen and BTE – Fruc, + ½% sucrose acclimated in separate tube from Maple tree sap | Mar. 1, 2016 pH on tape of 7. Mar. 6, 2016 | Maple tree sap in BTE, no | 2 straws in Holder #6 tank 1, and 1 | 3 pink soda straws that were ventilated, | Tubes store well but it is best to use |

TABLE 1-continued

| | | | | | |
|---|---|---|---|---|---|
| | BTE, at 44 F. in fridge for 10 minutes, combined, then packaged in 3 tubes, 75 ul capillary tube, caulked one end; placed in poultry straw, cotton down; inside ventilated soda straw. 3 straws made. 3 Pink straws. | pH on tape of 7.5. | fructose. | straws in Holder #5 tank 1. | 75 ul mylar capillary tube, inside poultry straw, inside ventilated soda straw. One sample was a capillary tube and soda straw only. | the soda straw and the mylar capillary tube only. |
| 85 | Semen and BTE – Fruc, + ½% sucrose acclimated in separate tube from Maple tree sap BTE, at 44 F. in fridge for 10 minutes, combined, then packaged in 3 tubes, 75 ul capillary tube, caulked one end; placed in poultry straw, cotton down; inside ventilated soda straw. 3 straws made. 3 Yellow straws. 10% Yolk Added to both mixes. | pH on pH tape was 7.0, pH on pH tape was 7.0 | Maple tree sap in BTE, no fructose/ with 10% Yolk. | 2 straws in Holder #6 tank 1, and 1 straws in Holder #5 tank 1. | 3 Yellow soda straws that were ventilated, 75 ul mylar capillary tube, inside poultry straw, inside ventilated soda straw. | |
| 86 | All volumes added together, No acclimation. Flash frozen. 10% Yolk Added. | | Maple tree sap in BTE, no fructose/ with 10% Yolk. | Holder #5, Tank 1. | 1 pink soda straw that was ventilated, 75 ul mylar capillary tube, inside a poultry straw, inside the soda straw. | |
| 87 | Acclimated for 10 minutes in the fridge at 43 F., and then flash frozen. 10% Yolk added. | pH of 7 on pH tape after thaw. | Maple tree sap in BTE no fructose with yolk. | Holder #6, in can #1. | Unknown color of soda straw. Was a Pink ventilated soda straw. | Stores well, but thaws too slow. |
| 88 | Acclimated for 10 minutes in the fridge at 43 F., and then flash frozen. 10% Yolk added. | 2016 pH on pH tape 7, pH on pH tape of 7 | Maple tree sap in BTE no fructose with yolk. | Holder #6, in can #1 has 2 pink straws, and Holder #5, | Two pink soda straws, ventilated, with a 75 ul mylar | Straws work well but insulate too well on thawing. |

TABLE 1-continued

| | | | | | |
|---|---|---|---|---|---|
| 89 | Acclimated for 10 minutes in the fridge at 43 F., and then flash frozen. 10% Yolk added. | 2016 pH on tape of 7.0 | Birch tree sap in BTE, No fructose, Plus YOLK | in can #1 has 1 pink straw. Holder #6 has 1 orange soda straw, and Holder #5 has 1 orange soda straw. | capillary tube inside a poultry straw. Two orange soda straws, ventilated, with 75 ul mylar capillary tubes inside poultry straws. | Does not explode but thaws too slowly. |
| 90 | Acclimated for 10 minutes in the fridge at 43 F., and then flash frozen. 10% Yolk added. | pH on tape of 7.0, 7.0, 7.0. | Birch tree sap in BTE, no fructose Plus Yolk. | Holder #6 has 2 green soda straws and Holder #5 has 1 green soda straw. | Three green soda straws, ventilated, with 75 ul mylar capillary tubes inside poultry straws. | Does not explode but thaws too slowly. |
| 91 | Temperature dropped only by using gel packs. | pH on tape after thaw was 7.5, 7.5 | MA only | Holder #4, Tank 1. 2 straws, one is green and the other deep purple. | 2 soda straws, one green and one deep blue. Ventilated with 75 ul mylar capillary tube inside a poultry straw. | |
| 92 | Temperature dropped only by using gel packs. | | MA only | Holder 3, Tank 1, 1 green soda straw. | 1 green soda straw, ventilated. With 75 ul mylar capillary tube inside a poultry straw. | Stores well, but thaws too slow. |
| 93 | Chilled at 45 F. for 10 minutes and then flash frozen. | pH on tape after thaw was 7.5, 7.5, 7.5. | MA only | Holder 4, Tank 1, 3 green soda | 3 green soda straws, ventilated, | |

TABLE 1-continued

| | | | | |
|---|---|---|---|---|
| | | | | straws all here with 75 ul mylar capillary tube inside a poultry straw. |
| 94 | Chilled at 45 F. for 10 minutes and then flash frozen. | DMA | Holder #5, Tank 1. | 1 orange soda straw with 2 poultry straws inside of it because I ran out of staples and had 1 soda straw left with a staple in it, marked with # 89 on it. |
| 95 | It was mixed at room temperature with no acclimation and then flash frozen. Lack of acclimation reduces cell survival. | 2016 pH 7 Purdy 10% Maple Tree Sap, 326 mOsm. | Holder 5 and 6, Tank 1. | 2 orange soda straws with 75 ul mylar capillary tubes inside poultry straws. Ventilated soda straw with poultry straw and mylar capillary tube inside that thaws too slowly. |
| 96 | It was mixed at room temperature with no acclimation and then flash frozen. | Purdy 10% Maple Tree Sap, 326 mOsm. | Holder # 5, Tank 1, Light yellow soda straw. | 1 light yellow soda straw with 75 ul mylar capillary tube inside a poultry straw. |
| 97 | It was mixed at room temperature, sandwiched between gel packs at 43 F., and then flash frozen. | pH of 7 on pH tape after thaw. Purdy 10% Maple Tree Sap, 326 mOsm. | Holder # 6, Tank 1. Pink soda straw. | 1 pink soda straw that was ventilated, 75 ul mylar capillary tube, inside a poultry straw, inside the soda straw. Stores well, but thaws too slow. |
| 98 | Purdy formulas begin with # 95. | | | |

TABLE 1-continued

| | | | | | |
|---|---|---|---|---|---|
| 99 | It was mixed at room temperature, sandwiched between gel packs at 43 F., and then flash frozen. | Feb. 24, 2016 Pink straw, no pH done, Second straw pH of 7.5, Last straw no pH done. | Purdy 20% Maple Tree Sap, 308 mOsm. | Holder #4 has 2 pink soda straws and Holder #5 has 1 pink soda straws. | 3 pink soda straws that are ventilated, 75 ul mylar capillary tube, inside a poultry straw, inside the soda straw. | |
| 100 | It was mixed at room temperature, sandwiched between gel packs at 43 F., and then flash frozen. | Mar. 6, 2016 pH 7 on tape after thaw. Mar. 6, 2016 pH of 7 on tape after thaw. | Purdy 20% Maple Tree Sap, 308 mOsm. | Three green soda straws in Holder #6, 1 straw in holder #5. | 4 greens soda straws that are ventilated, 75 ul mylar capillary tube, inside a poultry straw, inside the soda straw. | Good, stores well but thawed too slow. |
| 101 | It was mixed at room temperature, sandwiched between gel packs at 43 F. for 2 minutes, and then flash frozen. | Mar. 2, 2016 pH of 7 on pH tape after thaw. | Purdy 10% Maple tree sap | Two yellow straws, one in holder #6, and one in holder #5. | 2 Yellow soda straws that are ventilated, 75 ul mylar capillary tube, inside a poultry straw, inside a soda straw. | Soda straw did not have capillary tube in it, Lost in the tank. |
| 102 | It was mixed at room temperature, sandwiched between gel packs at 43 F. for 2 minutes, and then flash frozen. No acclimation. | Mar. 2, 2016 pH of 7; Mar. 6, 2016 pH of 7. | Purdy 5% Maple tree sap. | 3 orange soda straws, 2 in holder #6, and 1 in holder #5 | 3 orange soda straws that are ventilated, 75 ul capillary tube inside a poultry straw. | Good, stores well but thawed too slow. |
| 103 | It was mixed at room temperature, with no acclimation, and then flash frozen. | 7.5 and 7, 7, 7. | Purdy 10% Maple tree sap, plus 5% (13 ul) of DMA. | 4 green soda straws, 2 straws in holder #5 and 2 straws in holder #6. | 4 green soda straws that were ventilated, 75 ul mylar capillary tube, inside | Good |

TABLE 1-continued

| | | | | | |
|---|---|---|---|---|---|
| 104 | It was mixed at room temperature, with no acclimation, and then flash frozen. | 7 | Purdy 10% Maple tree sap plus Arabogalactin and then 12% MA. | Yellow straw in holder #5 | poultry straw, inside ventilated soda straw. Yellow soda straw that was ventilated, 75 ul mylar capillary tube, inside poultry straw, inside ventilated soda straw. | Good |
| 105 | Chilled 15 minutes and then second diluent added. Packaged quickly and then flash frozen. | 7.51 and 7.23. (adjusted wrong and bad for motility). | 2015 extenders that have sap in them. Second diluent had pH adjusted up with bicarb. | 2 straws in Holder #6, 1 straw in Holder #5 | Mylar capillary tube, caulked on one end, inside a small ventilated soda straw. | Stores well and thaws well. |
| 106 | Acclimated in the fridge at 42 F. for 15 minutes and then flash frozen. | 7.51 and 7.23. (adjusted wrong and bad for motility). | 2015 extenders that have sap in them. Second diluent had pH adjusted up with bicarb. | 2 straws in Holder #6 and 1 straw in Holder #5. | Mylar capillary tube, caulked on one end, inside a small ventilated soda straw. | Stores well and thaws well. |
| 107 | Acclimated 16 minutes at 42 F. and then packages into 3 straws and flash frozen. | pH 7.51 then pH 7.23 (adjusted wrong and bad for motility). | 2015 extenders that have sap in them. Second diluent had pH adjusted up with bicarb. | 2 straws in Holder #6 and 1 straw in Holder #5. | Mylar capillary tube, caulked on one end, inside a small ventilated soda straw. | Stores well and thaws well. |
| 108 | Acclimated 16 minutes at 42 F. and then packages | pH 7.51 then | 2015 extenders | 2 straws in Holder | Mylar capillary | Stores well and thaws |

TABLE 1-continued

| | | | | | |
|---|---|---|---|---|---|
| | into 3 straws and flash frozen. | pH 7.23 (adjusted wrong and bad for motility). | that have sap in them. Second diluent had pH adjusted up with bicarb. | #6 and 1 straw in Holder #5. | tube caulked one end with ventilated soda straw. | well. |
| 109 | Acclimated 16 minutes at 42 F. and then packages into 4 straws and flash frozen. | pH of 7.51 then pH of 7.23 (adjusted wrong and bad for motility). | 2015 extenders that have sap in them. Second diluent had pH adjusted up with bicarb. | 2 straws in Holder #6 and 2 straws in Holder #5. | Mylar capillary tube caulked one end with ventilated soda straw. | Stores well and thaws well. |
| 110 | Acclimated 16 minutes in the fridge at 42 F. and then flash frozen. | pH of 7.51 then pH of 7.23 (adjusted wrong and bad for motility). | 2015 extenders that have sap in them. Second diluent had pH adjusted up with bicarb. | 2 straws in Holder #6 and 1 straw in Holder #5. | Mylar capillary tube caulked one end with ventilated soda straw. | Stores well and thaws well. |
| 111 | Acclimated for 18 minutes at 42 F. in the fridge and then flash frozen. | pH of 7.51 then pH of 7.23 (adjusted wrong and bad for motility). | 2015 extenders that have sap in them. Second diluent had pH adjusted up with bicarb. | 2 straws are in Holder #6 and 1 straw is in Holder #5. | Mylar capillary tube caulked one end with ventilated soda straw. | Stores well and thaws well. |
| 112 | Acclimated on gel packs at 42 F. for 16 minutes. Then flash frozen. One sample got caught on the holder and stayed above the LN2 and was not flash frozen. The other samples in the group were flash frozen and died. | 7.4 then 7.23 both 2015 diluents with sap that both had pH adjustments that went bad. | BTE minus fructose, plus ½% sucrose with pH adjusted with bicarb from 7.51 to 7.4.; | 1 straw in holder #5 and 2 straws in holder #4. | Mylar capillary tube caulked one end with ventilated soda straw. | Caulk tends to come out on thaw due to LN2 pressure inside the capillary tube. |

TABLE 1-continued

| | | | | |
|---|---|---|---|---|
| 113 | Acclimated for 16 minutes in the fridge at 42 F. and then flash frozen. | 7.4 then 7.23 both 2015 diluents with sap that both had pH adjustments that went bad. | BTE minus fructose, plus ½% sucrose with pH adjusted with bicarb from 7.51 to 7.4.; Then added BTE - Fructose + Maple Tree Sap tree #3 with pH adjusted with bicarb to 7.23. | 1 straw in holder #5 and 2 straws in holder #4. | Mylar capillary tube caulked one end with ventilated soda straw. | Stores well and thaws well. |
| 114 | Acclimated for 16 minutes in the fridge at 42 F. and then flash frozen. | 7.4 then 7.23 both 2015 diluents with sap that both had pH adjustments that went bad. | BTE minus fructose, plus ½% sucrose with pH adjusted with bicarb from 7.51 to 7.4.; Then added BTE - Fructose + Maple Tree Sap | 1 tube in Holder #5 and 1 tube in Holder #4. | Mylar capillary tube caulked one end with ventilated soda straw. | |

TABLE 1-continued

| | | | | | |
|---|---|---|---|---|---|
| 115 | Acclimated 20 minutes and then flash frozen. | | tree #3 with pH adjusted with bicarb to 7.23. | | |
| 116 | Acclimated 15 minutes and then flash frozen. | pH 6.27 then pH 6.74. | Amur Maple + BTE − Fruc with adjusted pH of 6.74 with Glutathione + NN-Bis . . . Sulfonic Acid. | 3 straws in Holder #3. | Mylar capillary tube caulked one end with ventilated soda straw. | Stores well and thaws well. |
| 117 | Acclimated 15 minutes and then flash frozen. | pH 6.27 then pH 6.74. | Amur Maple + BTE − Fruc with adjusted pH of 6.74 with Glutathione + NN-Bis . . . Sulfonic Acid. | 4 straws in Holder #3. | Mylar capillary tube caulked one end with ventilated soda straw. | Stores well and thaws well. |
| 118 | Acclimated semen in its own tube for 5 minutes and then added in the Maple tree sap tree #3 (2015). Then slowly lowered into LN2. | pH 6.48 | BTE − Fructose + Maple Tree #3 sap, 2015. (original 6.48 pH from 2015) | 2 straws in holder #3. | Mylar capillary tube + Critocap + Blue cap + Ventilated soda straw. | |
| 119 | Put in holder #5 above liquid nitrogen vapors for 10 seconds and then flash froze with slow immersion. | 7.51. then 6.48 | BTE − Fructose + ½% Sucrose (pH 7.51), then BTE − Fructose + Maple Tree #3 sap, 2015. (pH 6.48). | #5 | Mylar capillary tube, caulked on one end, inside a small ventilated soda straw. | Caulk tends to come out on thaw due to LN2 pressure inside the capillary tube. |

TABLE 1-continued

| | | | | | |
|---|---|---|---|---|---|
| 120 | Acclimated 15 minutes at 42 F. then hung over the vapors 15 seconds and then slowly lowered into LN2. | 7.51 then 6.48 | BTE - Fructose + ½% Sucrose (pH 7.51); then BTE - Fructose + Maple Tree #3 sap, 2015, (pH 6.48). | 4 straws in Holder #3. | Mylar capillary tube, caulked on one end, inside a small ventilated soda straw. | Caulk tends to come out on thaw due to LN2 pressure inside the capillary tube. |
| 121 | Acclimated 15 minutes at 42 F. then hung over the vapors 15 seconds and then slowly lowered into LN2. | 7.51 then 6.48 | BTE - Fructose + ½% Sucrose (pH 7.51); then BTE - Fructose plus Maple Tree sap #3 2015 (pH 6.48) | 2 straw in Holder #3. | Natellson Capillary tube with 1 cap in a large ventilated soda straw. (Orange). | |
| 122 | Acclimated 15 minutes at 42 F. then hung over the vapors 15 seconds and then slowly lowered into LN2. | pH 7.51 then pH 6.48. | BTE - Fruc + ½% Suc (pH 7.51); then BTE - Fruc + 1st Run Maple tree sap. 2015 | 1 straw in Holder #3. | Natellson capillary tube + cap + Large ventilated soda straw (Green). | |
| 123 | | | | | | |
| 124 | | | | | | |
| 125 | | | | | | |
| 126 | Acclimated for 15 minutes at 42 F. in the fridge, and then flash frozen in LN2. | pH 7.51 then pH 6.48. | BTE - Fructose + ½% Sucrose 2015 (pH 7.51); then added BTE - Fructose + Maple Tree Sap tree #3 2015 (pH 6.48) | Three straws in Holder #5, 1 Straw in Holder #4. | Mylar capillary tube caulked one end with ventilated soda straw. | Caulk tends to come out on thaw due to LN2 pressure inside the capillary tube. |

TABLE 1-continued

| | | | | |
|---|---|---|---|---|
| 127 | | pH 7.56 then pH 6.48 | #4 | Mylar capillary tube caulked one end with ventilated soda straw. |
| 128 | Acclimated for 15 minutes then suspended over LN2 vapors for 15 seconds and then slowly lowered into LN2. | pH 7.56 then pH 6.48 | BTE - Fructose plus 1st run Alaska Birch (pH 7.56) and then BTE - Fructose + Maple Tree #3 2015 (pH 6.48) | 3 straws in Holder #4. | Mylar capillary tube caulked one end with ventilated soda straw. Caulk tends to come out on thaw due to LN2 pressure inside the capillary tube. |

I claim:

1. A method of cryogenically preserving sperm comprising:
   a. combining sperm to be cryogenically preserved and a composition that comprises (1) a cryoprotectant, comprising one or more tree saps; and (2) an extender medium to produce a sperm/medium combination; and
   b. subjecting the combination to conditions that result in cryopreservation of sperm, thereby producing a cryopreserved combination that comprises cryopreserved sperm,
   wherein the sperm to be cryogenically preserved is avian sperm or non-human mammalian sperm, and
   wherein the one or more tree saps is cold-hardy maple tree sap, birch tree sap, or a combination thereof.

2. The method of claim 1 wherein the cryopreserved sperm of step (b) demonstrates survival up to 73%.

3. The cryopreserved combination resulting from the method of claim 2.

4. The method of claim 1 wherein the cryopreserved sperm of step (b) demonstrates motility at greater than 30% and up to about 60% after thawing.

5. The cryopreserved combination resulting from the method of claim 4.

6. The method of claim 1 wherein the one or more tree saps is the only cryoprotectant.

7. The method of claim 1 wherein an additional cryoprotectant is added.

8. The method of claim 1 wherein the sperm is avian sperm.

9. The method of claim 1 wherein the sperm is derived from the Northern goshawk (*Accipiter gentilis*).

10. The method of claim 1 wherein the sperm is derived from a non-human mammal.

11. The method of claim 1 wherein the sperm is derived from an animal type selected from the group consisting of canine, avian, cattle, porcine, and equine.

12. The method of claim 1 wherein the one or more tree saps is a first run sap.

13. The method of claim 1 wherein the extender medium does not contain fructose.

14. The method of claim 1 wherein the method comprises the additional step of subjecting the combination to a temperature between −80° C. and −198° C. for a period of at least one day.

15. The cryopreserved combination resulting from the method of claim 1.

16. A method of fertilizing an egg cell comprising the steps of thawing a cryopreserved combination produced by the method of claim 1, and introducing the combination to an unfertilized egg cell, wherein the egg cell becomes fertilized.

17. The method of claim 16, wherein the egg cell that is fertilized with the cryopreserved semen is an avian egg.

18. The method of claim 16, wherein the egg cell that is fertilized with the cryopreserved semen is a mammalian egg.

19. A composition comprising tree sap, semen, and extender medium.

20. The composition of claim 19, wherein the sap is at least 50% by volume of the composition.

21. The composition of claim 19, wherein the composition is placed within a container, wherein the container is selected from the group consisting of a vial and a straw.

22. The composition of claim 19, wherein the tree sap is selected from birch or maple sap.

* * * * *